United States Patent [19]
Montejo et al.

[11] Patent Number: 5,161,222
[45] Date of Patent: Nov. 3, 1992

[54] SOFTWARE ENGINE HAVING AN ADAPTABLE DRIVER FOR INTERPRETING VARIABLES PRODUCED BY A PLURALITY OF SENSORS

[75] Inventors: Leopoldo S. Montejo; Martine Pean, both of Paris, France

[73] Assignee: Human Microprocessing, Inc., Milwaukee, Wis.

[21] Appl. No.: 569,857

[22] Filed: Aug. 20, 1990

[51] Int. Cl.⁵ ............................................. G06F 13/14
[52] U.S. Cl. .................... 395/500; 364/934.0; 364/934.2; 364/934.3; 364/935.42; 364/940.9; 364/940.1; 364/942.4; 364/DIG. 2
[58] Field of Search ............... 395/500, 325, 700; 364/146, 147, 188, 189, 138, 139, 200 MS File, 900 MS File

[56] References Cited

U.S. PATENT DOCUMENTS

| | | | |
|---|---|---|---|
| 4,481,574 | 11/1984 | De Fino et al. | 364/200 |
| 4,570,217 | 2/1986 | Allen et al. | |
| 4,589,063 | 5/1986 | Shah et al. | 395/275 |
| 4,649,479 | 3/1987 | Advani et al. | 395/700 |
| 4,663,704 | 5/1987 | Jones et al. | 364/188 |
| 4,672,532 | 6/1987 | Jonge Vos | 395/600 |
| 4,701,848 | 10/1987 | Clyde | 395/325 |
| 4,734,854 | 3/1988 | Afshar | 364/200 |
| 4,858,101 | 8/1989 | Stewart et al. | 364/131 |
| 5,014,185 | 5/1991 | Saito et al. | 364/188 |

OTHER PUBLICATIONS

Armbrust et al., "Forward Looking DVI," *PC Tech Journal*, vol. 3, No. 9, Sep. 1985, pp. 42-55.

*Primary Examiner*—Thomas C. Lee
*Assistant Examiner*—William M. Treat
*Attorney, Agent, or Firm*—Godfrey & Kahn

[57] ABSTRACT

A method for interpreting variables produced by a sensor which communicates by a means of serial analog protocols including interpreting an external process request for data information from the sensor; overlaying a predetermined adaptable driver which when adjusted in a predetermined fashion corresponds to the characteristics of the sensor; polling or listening to the sensor thereby receiving the data information requested; and transmitting the information to a predetermined destination.

14 Claims, 18 Drawing Sheets

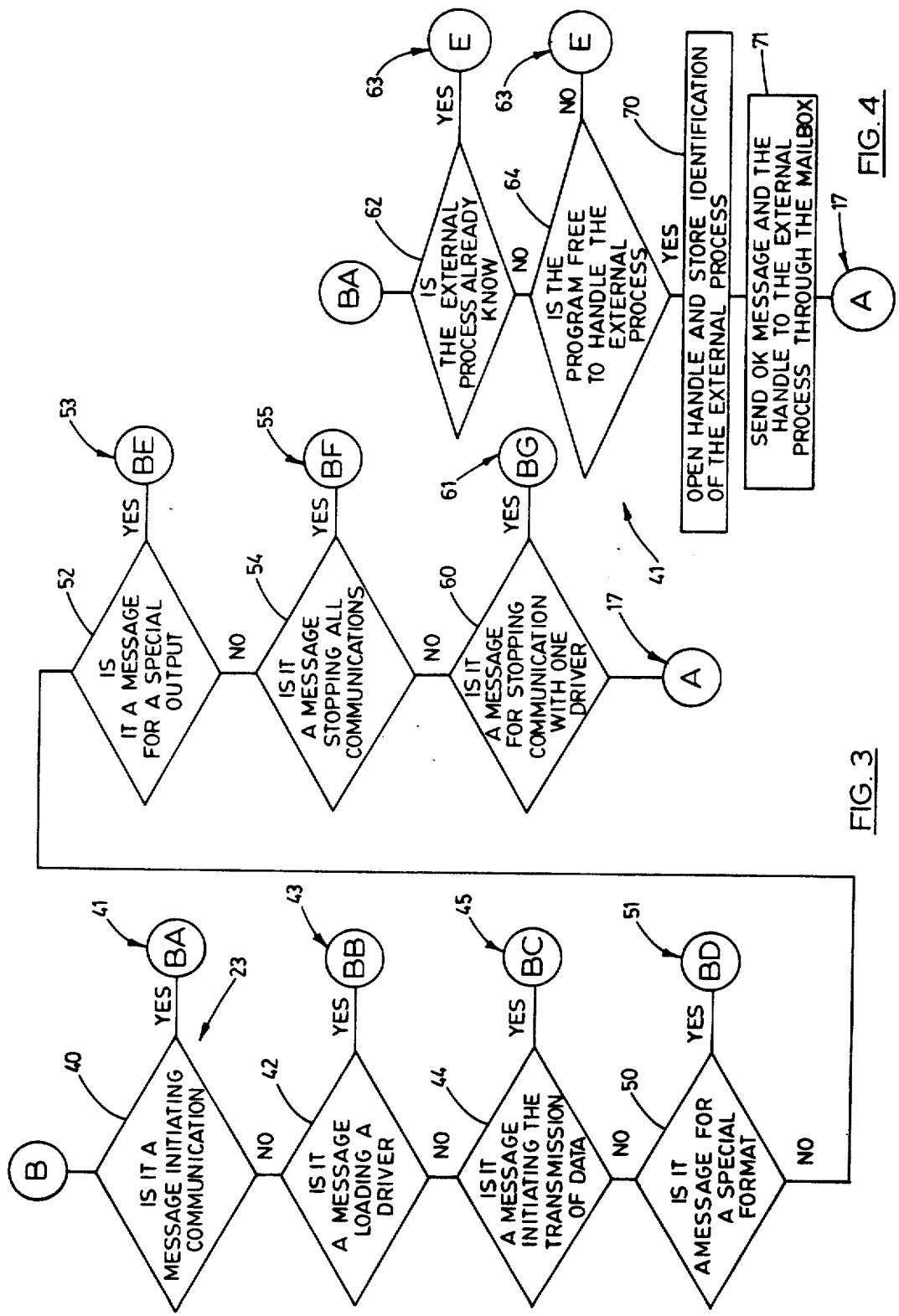

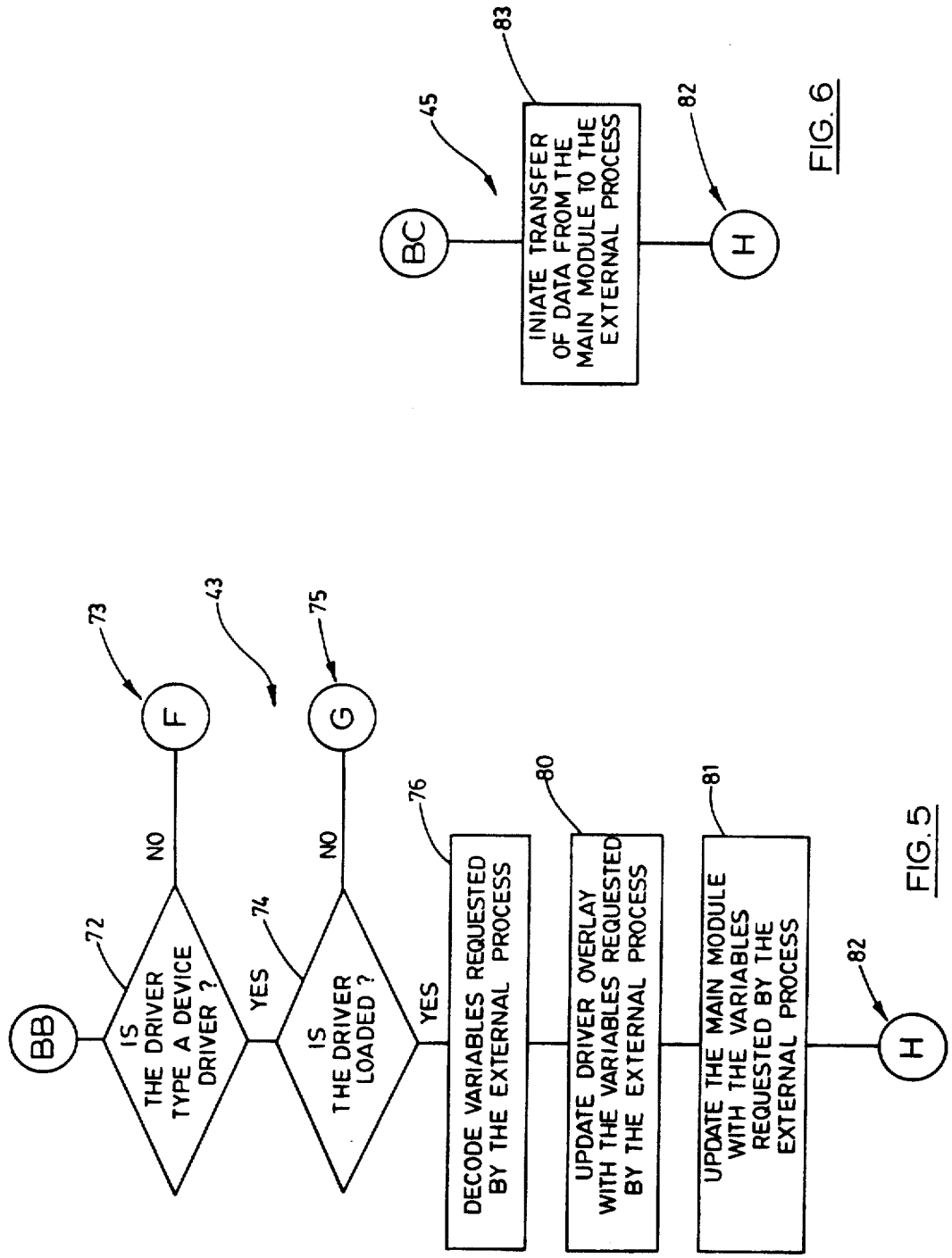

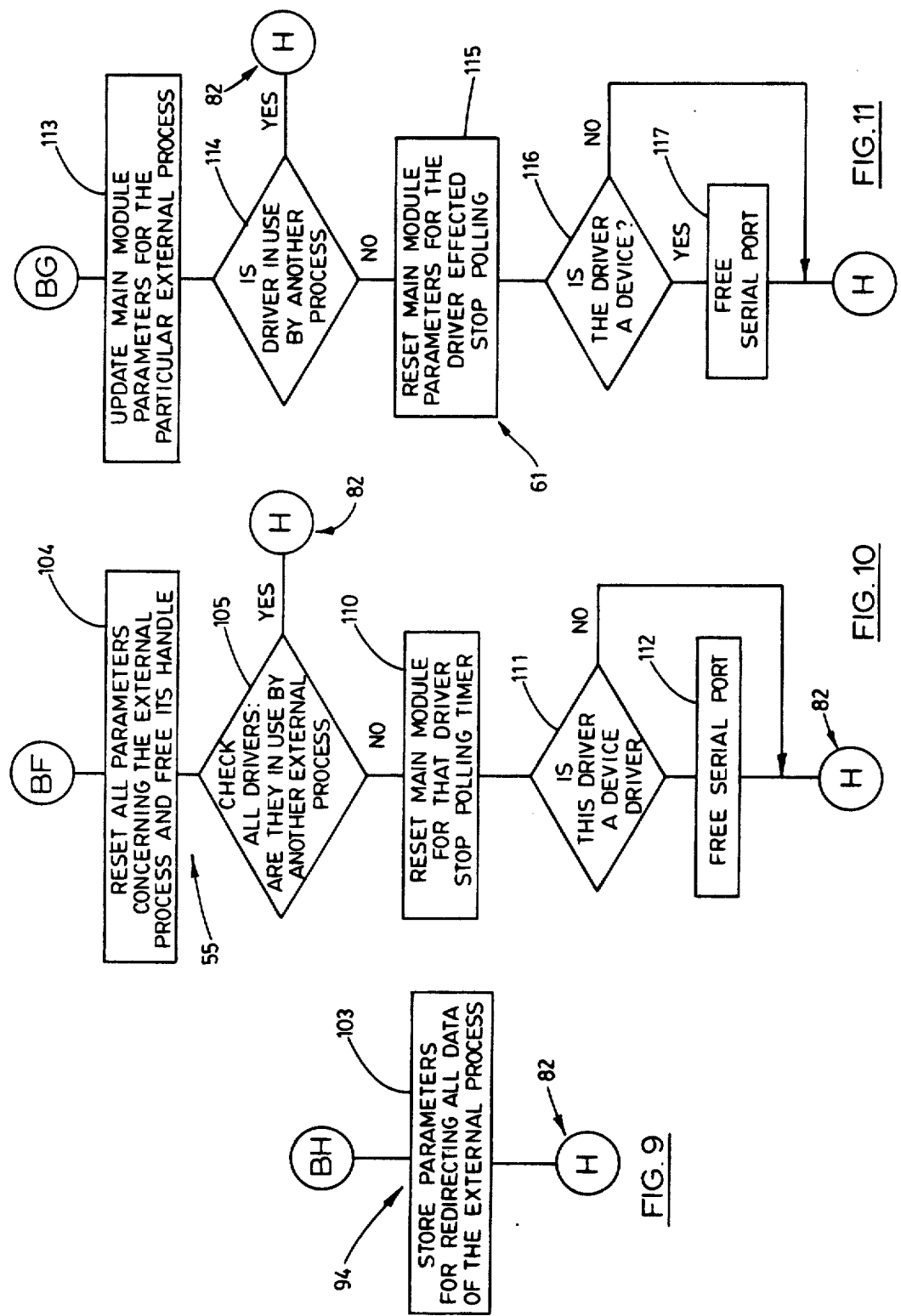

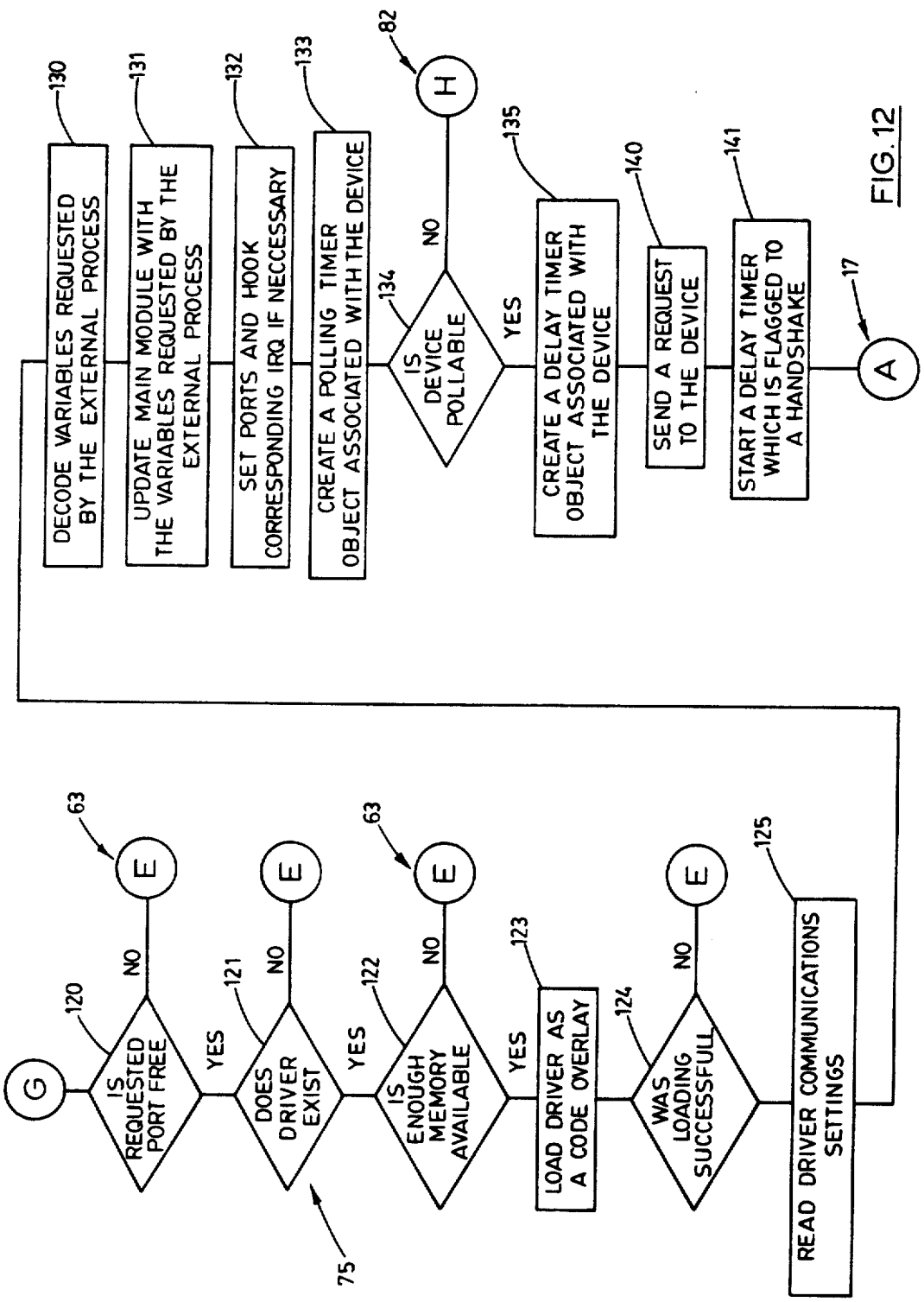

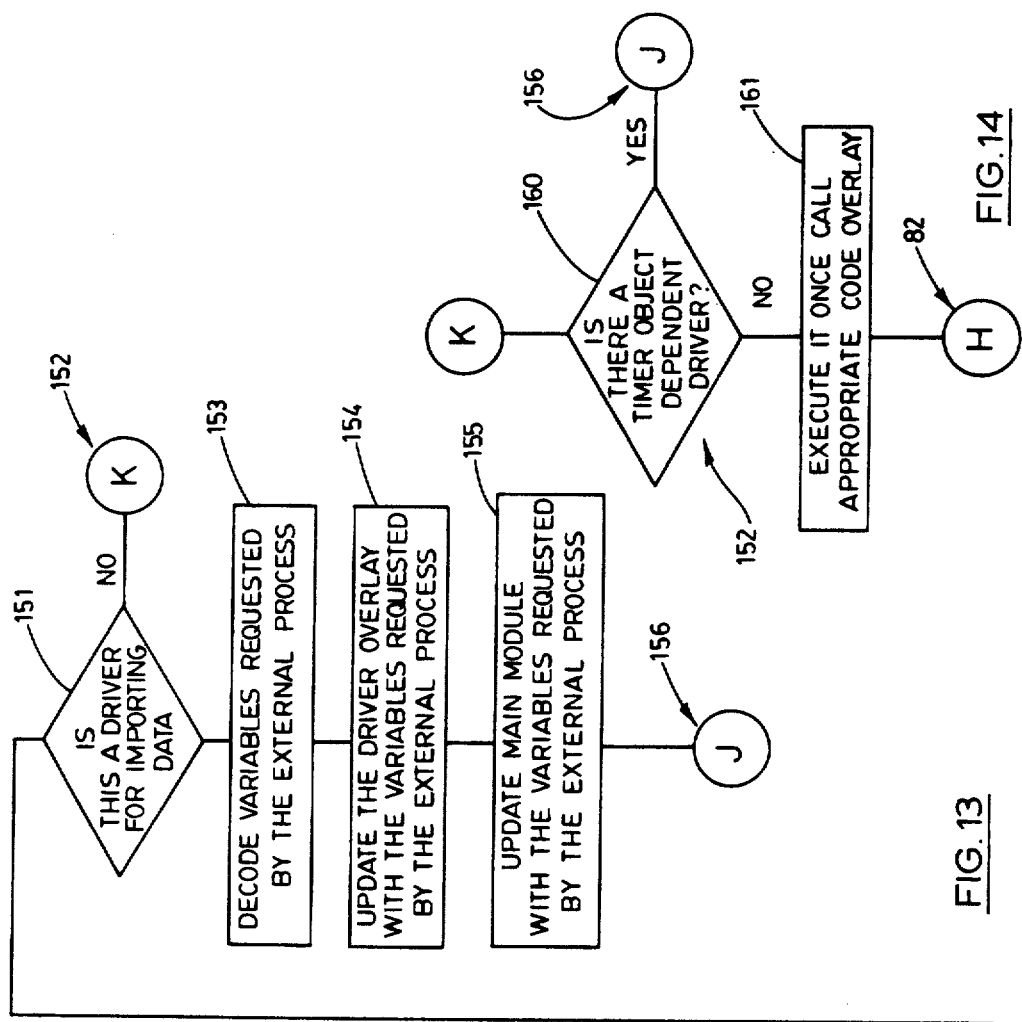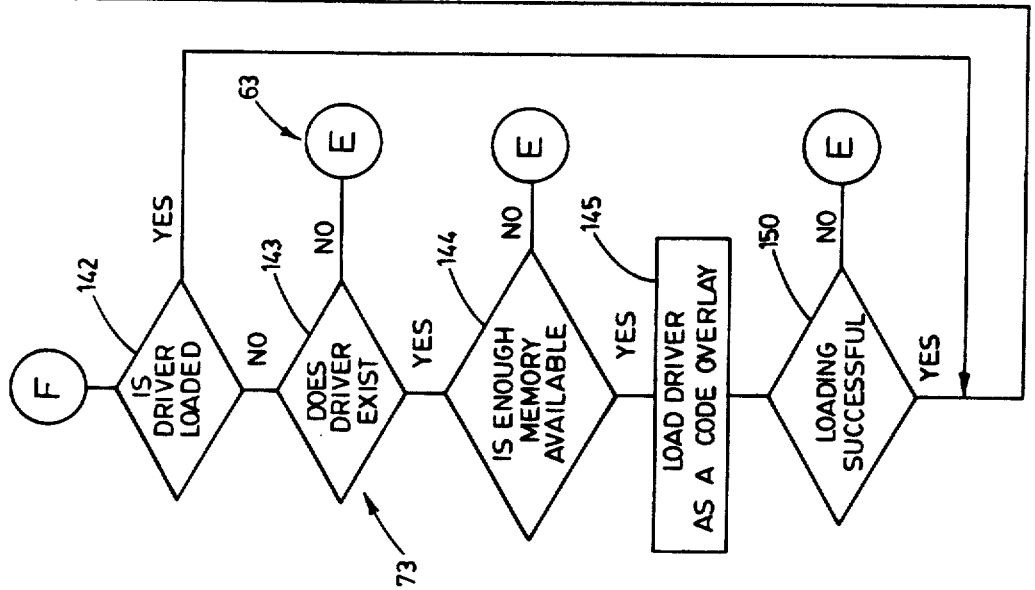

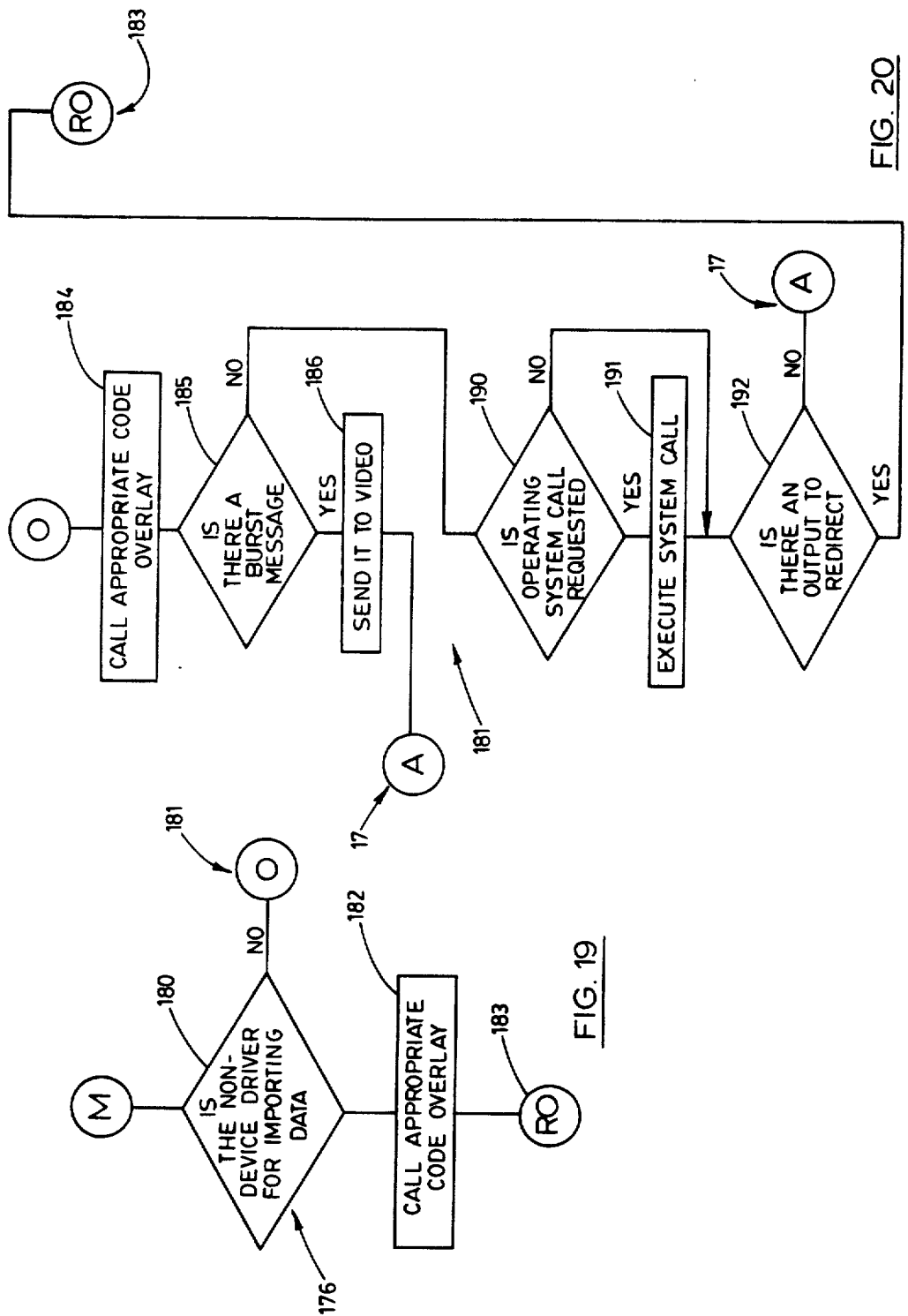

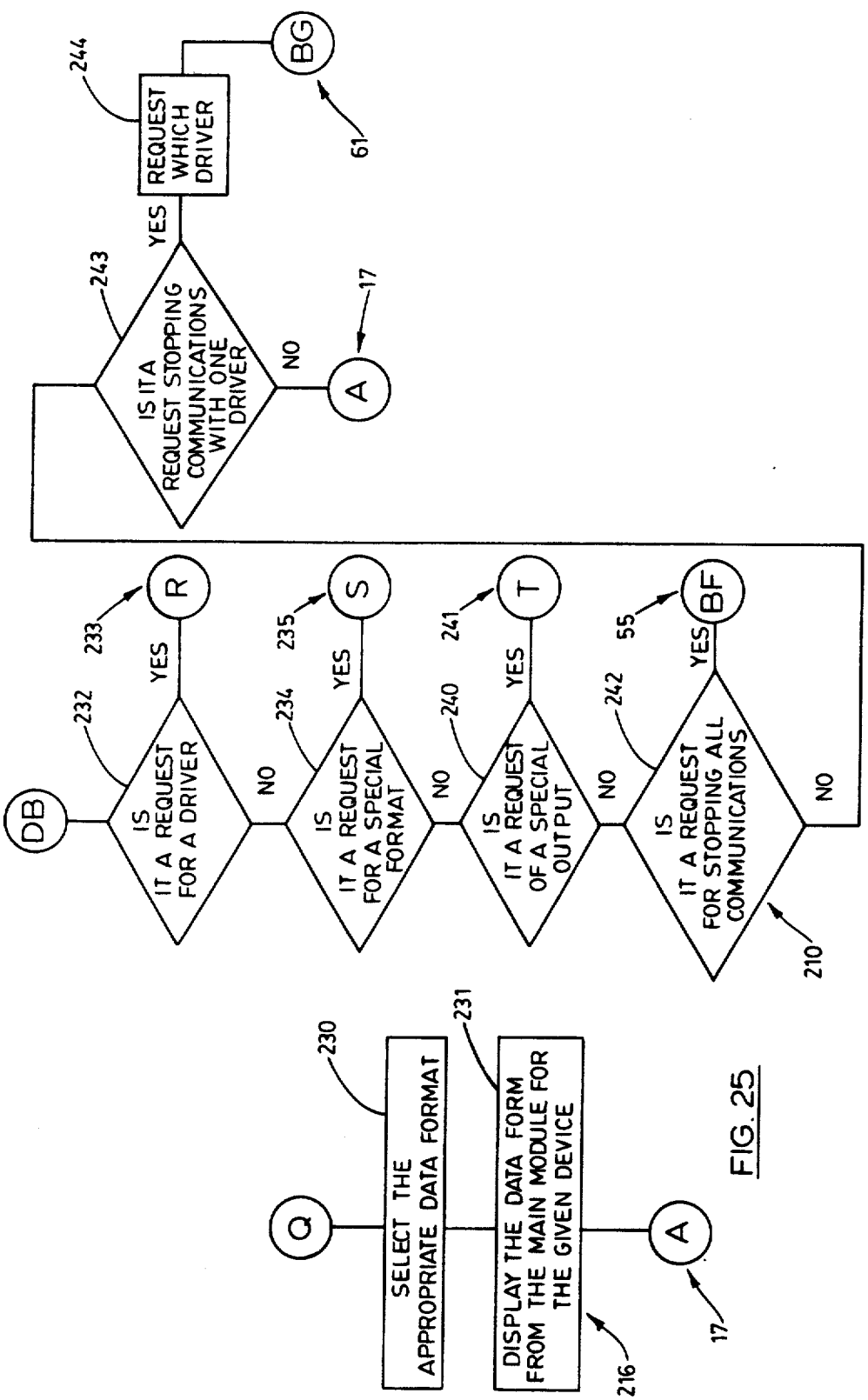

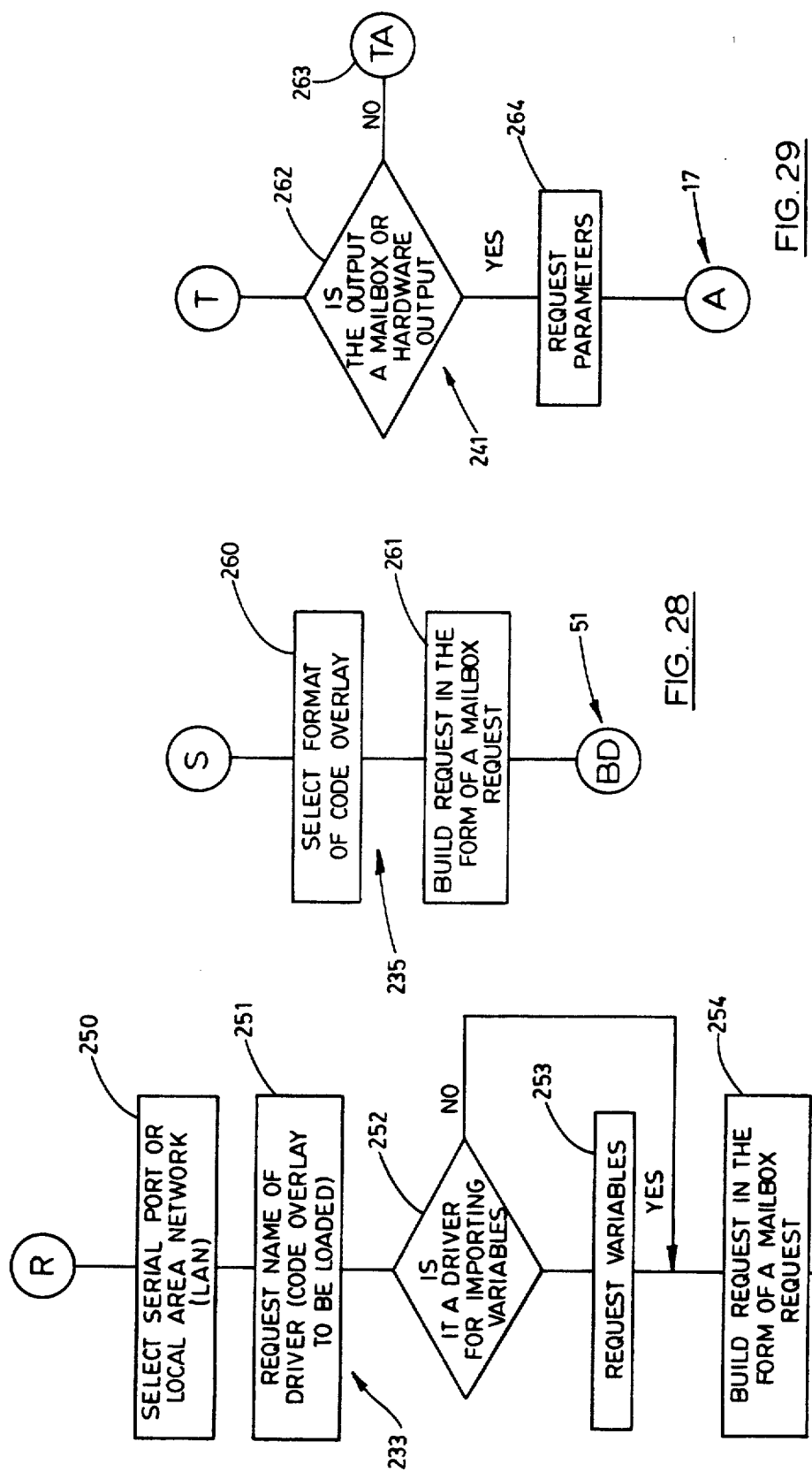

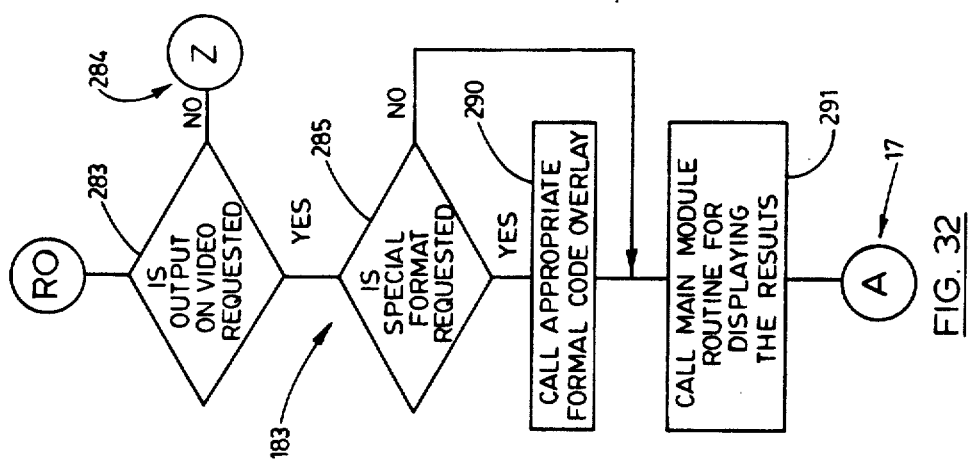
FIG. 32
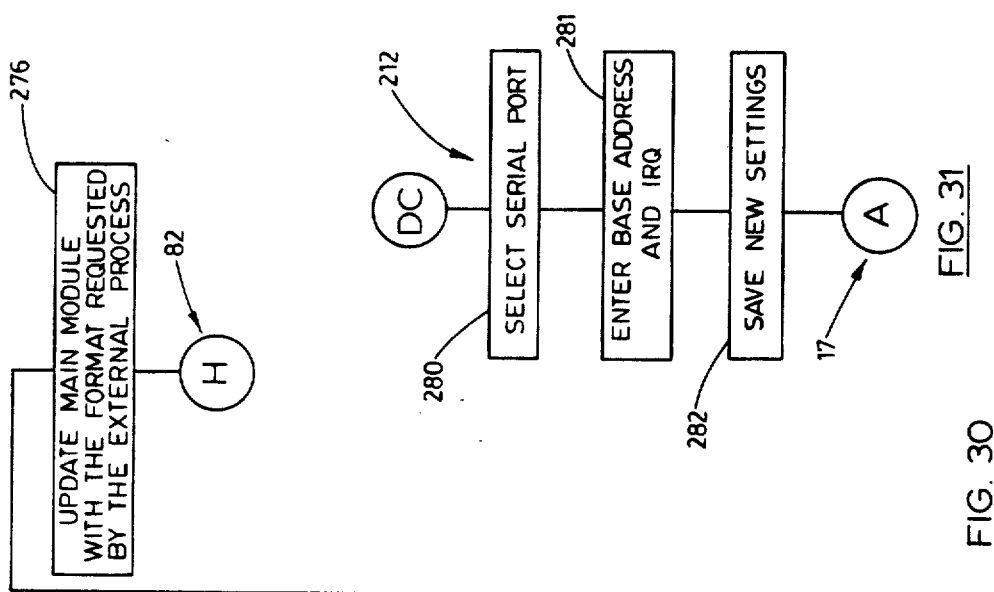
FIG. 31
FIG. 30
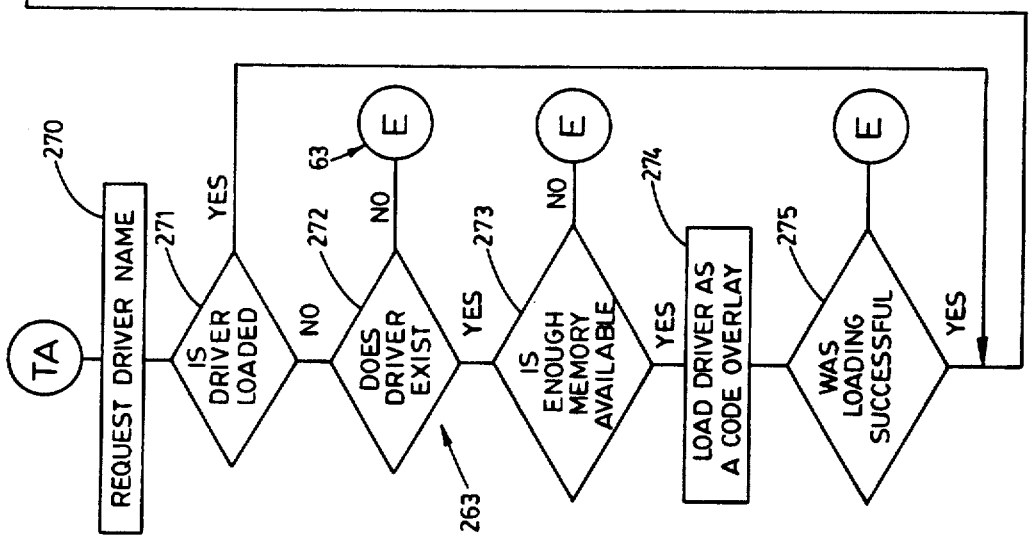

SOFTWARE ENGINE HAVING AN ADAPTABLE DRIVER FOR INTERPRETING VARIABLES PRODUCED BY A PLURALITY OF SENSORS

BACKGROUND OF THE INVENTION

1. Field of the Invention

The present invention relates to a method for interpreting variables produced by a plurality of sensors and more particularly to such a method adapted for use in communicating with sensors which are made integral with medical monitoring equipment, and which communicate by means of serial or analog protocols, and wherein the method provides a rapid means by which a user, such as a clinician, may interface with diverse monitors and thereafter receive the information produced by the monitors in a predetermined format and at a predetermined destination.

2. Description of the Prior Art

The medical profession has long sought an effective method for receiving and thereafter evaluating clinical information which may be produced by various types of medical monitoring equipment or other diagnostic equipment and which could, for example be located in remote locations such as in a laboratory which is located in another area of a hospital. Further, the medical profession has long sought an effective method whereby this clinical information may be both freely exchanged to those individuals having a need to know same, such as hospital administrators, records clerks, and laboratory technicians, as well as have the information available for storage or transmission to any number of predetermined locations such as printers, video monitors, modems or local area networks, as conditions warrant. As should be understood the various medical monitoring equipment and other diagnostic devices used in laboratories and other clinical setting such as surgical suites, emergency rooms, etc. while having some similar component, have typically communicated with automated control assemblies, such as personal computers, by means of serial or analog protocols which have varied somewhat from one to the other. Therefore, software programs have been developed which have provided a means by which such information may be converted into a common format such as an interpretable ASCII data and thereafter exported or imported into another program for use therein. However, it should be readily recognized that the importation and exportation of interpretable ASCII data and the reformatting of same for use with a new software program is quite often time consuming and further may cause other problems which have detracted from the usefulness of this same technique.

The inconveniences and hardships occasioned to a patient by the delays which occur as a consequence of a clinician reviewing clinical data which may be produced by a plurality of medical sensors or other diagnostic equipment which may be positioned in remote location is readily apparent. Frequently, the information is received in piecemeal fashion and in various formats which require some time for evaluation. Further comparing and contrasting of the information is often necessary to determine the proper therapy for the malady under consideration. In addition to the foregoing the information has not, heretofore, been available to a clinician at a centralized location whereby the clinician can easily review same quickly and efficiently.

While the prior art has suggested various control assemblies including software programs which have provided a means by which particular clinical information such as medical history files, may be entered and thereafter used at diverse locations by clinicians and others for diagnostic and other purposes, such software programs have typically been cumbersome, complex and have not included a convenient means by which sensor information produced by a device which is foreign to the software program structure can be rapidly interfaced with the software program with a minimal amount of reprogramming of same.

Therefore it has long been known that it would be desirable to have a method and apparatus for interpreting variables produced by a plurality of sensors which communicate by means of serial or analog protocols and which can be employed in a wide variety of different institutional environments, and without the need for substantial alteration or rewriting of software programs which interface with same, and which can be manufactured and purchased at a relatively moderate cost, and which is both highly efficient in operation, and which further reduces to an absolute minimum the assorted problems associated with the monitoring and interpretation of clinical information which may be produced by a plurality of monitors and other diagnostic devices which may be positioned in remote locations.

SUMMARY OF THE INVENTION

Therefore, it is an object of the present invention to provide an improved method for interpreting variables produced by a plurality of sensors, such as medical monitoring equipment and other diagnostic devices and the like.

Another object of the present invention is to provide a method for interpreting variables produced by a plurality of sensors, and particularly to a method which has utility when used in combination with a plurality of medical sensing devices, and which is adapted in response to an external process request to receive information from the medical sensors, and transmit same to a predetermined destination.

Another object of the present invention is to provide such a method which is operable to obtain the individual benefits to be derived from related prior art methods and devices while avoiding the detriments individually associated therewith.

Another object of the present invention is to provide such a method which is particularly well suited when used, in combination with medical monitoring equipment, to provide a clinician with assorted information relative to a patient's condition at a centralized location and which further may be easily reprogrammed in a fashion to permit the information to be transmitted to a plurality of predetermined destinations such as video monitors, printers, modems, local area networks, and the like.

Another object of the present invention is to provide such a method which is operable to deliver information regarding a patient's condition rapidly, dependably and efficiently while reducing to an absolute minimum the possibility of malfunction.

Another object of the present invention is to provide such a method which is of relatively moderate cost to purchase and maintain and which further is relatively inexpensive to operate.

Another object of the present invention is to provide such a method which is operating system independent, and which is operable to interface with conventional software programs for purposes of further increasing the speed and efficiency with which the given information produced by a plurality of medical sensors can be produced during a predetermined time period.

Another object of the present invention is to provide such a method which is characterized by ease of employment, relative simplicity in its architecture, and which can be sold at a moderate price.

Another object of the present invention is to provide such a method which allows an operator to communicate with, and receive information from, a medical sensor foreign to the present invention, the present method including a means by which the operator may rapidly program the invention to receive the information produced by the foreign sensor.

Still another object of the present invention is to provide a method which may be manufactured as a software program or alternately manufactured as an integral subassembly of a piece of hardware such as in the nature of a computer chip which may be employed in a personal computer or which further may be manufactured in the manner of a retrofit.

Further objects and advantages of the present invention are to provide improved elements and arrangements thereof in a method for the purposes described which are dependable, economical, durable and fully effective in accomplishing its intended purposes.

These and other objects and advantages are achieved in a method for interpreting variables produced by a sensor which communicates by means of serial or analog protocols including interpreting an external process request for data information from the sensor, overlaying a predetermined adaptable driver which, when adjusted in a predetermined fashion, corresponds to the characteristics of the sensor, polling or listening to the sensor thereby receiving the data information requested, and transmitting the information to a predetermined destination.

BRIEF DESCRIPTION OF THE DRAWINGS

FIG. 3 illustrates in detail the mailbox object process shown in FIG. 2.

FIG. 4 sets forth in greater detail the mailbox object process shown in FIG. 3.

FIG. 5 sets forth in greater detail the operation of the mailbox object process shown in FIG. 3.

FIG. 6 illustrates in greater detail the mailbox object process shown in FIG. 3.

FIG. 9 sets forth the subroutine for storing the parameters for redirecting all data of the external process and which is shown in FIG. 8.

FIG. 10 sets forth in greater detail the mailbox object process and more particularly the operation for stopping all communications and which is shown in FIG. 3.

FIG. 11 sets forth in greater detail the mailbox object process and more particularly the operation for stopping all communications with one driver and which is shown in FIG. 3.

FIG. 12 sets forth in greater detail the mailbox object process and more particularly the operation which is undertaken following a determination that a driver is not loaded and which is shown in FIG. 5.

FIG. 13 sets forth in greater detail the mailbox object process and more particularly the operation which is undertaken once it is determined that a device driver is being employed and which is shown in FIG. 5.

FIG. 14 shows in further detail the mailbox object process and more particularly the operation following a determination that the driver is operable to import data and which is shown in FIG. 13.

FIG. 19 sets forth in further detail the object timer process of the present invention and more particularly the operation of determining whether the driver type is a device driver and which is shown in FIG. 18.

FIG. 20 sets forth in further detail the object timer process of the present invention and more particularly the operation following a determination that a non-device driver is not being utilized for importing data and which is shown in FIG. 19.

FIG. 25 sets forth in further detail the keyboard object process, and more particularly the operation following a determination that a device is not an input device as shown in FIG. 24.

FIG. 26 sets forth in further detail the keyboard object process, and more particularly the operation following a determination that keyboard interaction with the main module is requested and which is shown in FIG. 23.

FIG. 27 sets forth in further detail the keyboard object process, and more particularly the operation following a determination that a message is a driver request and which is shown in FIG. 26.

FIG. 28 sets forth in further detail the keyboard object process, and more particularly the operation following a determination that a message for a special format has been received and which is shown in FIG. 26.

FIG. 29 sets forth in further detail the keyboard object process, and more particularly the operation following a determination that a message is for a special output and which is shown in FIG. 26.

FIG. 30 sets forth in further detail the keyboard object process, and more particularly the operation following a determination that an output is not a mailbox or hardware output as shown in FIG. 29.

FIG. 31 sets forth in further detail the keyboard object process, and more particularly the operation following a determination that port assignments have been requested and which is shown in FIG. 23.

FIG. 32 sets forth in further detail the keyboard object process, and more particularly the operation for calling an appropriate code overlay and which is best illustrated by reference to FIG. 19.

DETAILED DESCRIPTION OF THE PREFERRED EMBODIMENT

Figure 2:
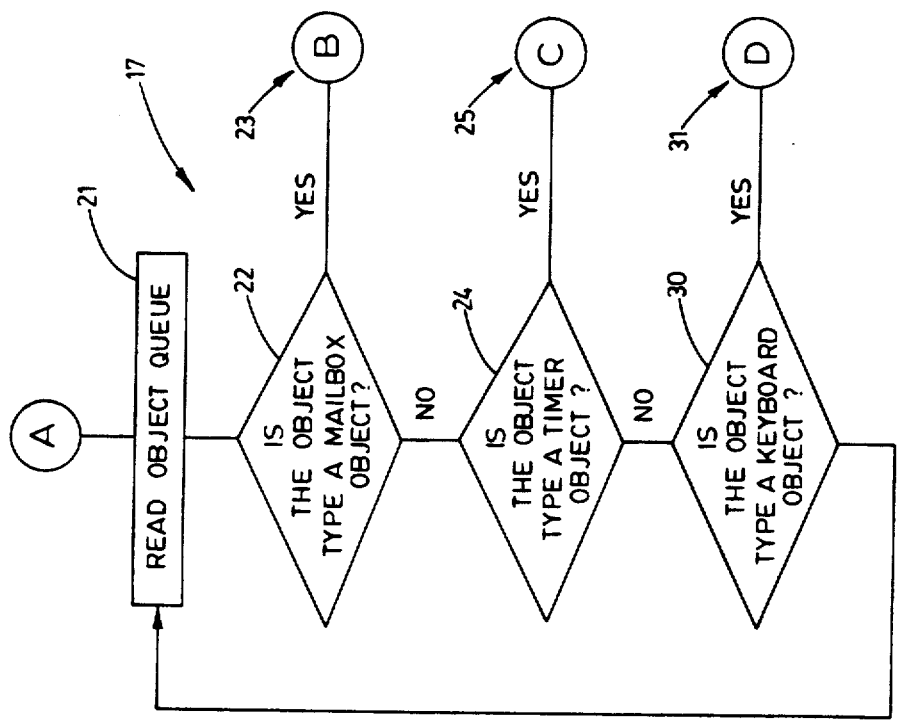
FIG. 2 sets forth in detail the operation of the object queue loop of the present invention.

The present invention provides a method for interpreting variables produced by a plurality of sensors and which communicate by means of serial or analog protocols, and more particularly to such a method for receiving, decoding, and delivering at a predetermined location, data information which is produced by a plurality of medical sensing devices and other diagnostic equipment and which is used by a clinician in the diagnosis of various maladies which affect a patient. As should be understood the hardware components which employ the present invention include a personal computer, medical monitoring equipment, and other devices such as local area networks, modems, computer printers, video monitors and hard disk storage devices, which are pictorially illustrated in FIG. 34 and which are well understood by those skilled in the art.

In accordance with the primary aspect of the above-identified method and which is operable to interpret variables produced by a plurality of sensors, it should be understood that the present method is an operating system independent software engine which is operable to read the variables from any medical device which communicates by means serial or analog protocols. Due in large measure to its relatively open architecture, the present method is also capable of processing data information received from any local area network and then treat this same information as if it was in fact a device. In addition to the foregoing, the present method is operable to transmit data in a user defined format to a multiplicity of different devices which may include computer printers, video monitors and hard disk storage devices as conditions warrant.

The present invention is operable, in summary, to read, decode, reformat, and output information from any medical sensing device, modem, or local area network and then redirect this information, which is in a predetermined user defined format, to any printer, software mailbox, serial port, hard disk, local area network or video monitor. This is graphically illustrated in FIG. 34. In short, the present method is operable to act as a bridge or as a link between a clinician and a multiplicity of devices or sensors and further is adapted to interface with medical devices that are even presently non-existent today. This is achieved by means of an adaptable code overlay or skeleton which will be discussed in greater detail hereinafter.

To achieve the beneficial results discussed above, the present method, which includes a software engine, has several features which will be discussed, in general, in the paragraphs which follow. More particularly the software engine of the present invention has several features which are noteworthy, for example, The software engine of the present invention is:

1. Object oriented with respect to four critical elements, these include time, mailboxes, keyboard and object queue.

2. The software engine interprets requests from an external calling process.

3. The software engine in response to the external calling process overlays an appropriate driver in response to the external calling process request.

4. The software engine actuates, as appropriate, the hardware communication interrupts if necessary.

5. The software engine polls [or listens to] the device, local area network, modem or other diagnostic equipment, as appropriate.

6. The software engine is operable, upon receiving the information from the device, local area network, modem or other diagnostic equipment to prepare an answer, in a user definable way, by means of a software overlay thereby providing a clinician with information in a format which assists him/her in an appropriate diagnosis of the patient's malady.

7. The software engine is adapted to output, upon the request of the user, to a requested mailbox, serial port, printer, local area network, or video monitor as appropriate.

In the paragraphs which follow the general characteristics of the software engine will be discussed. Further, an explanation will be provided regarding how messages are received by the software engine, and how same are decoded, reformatted and transmitted to a predetermined destination based on user commands supplied by the external process.

Figure 34:
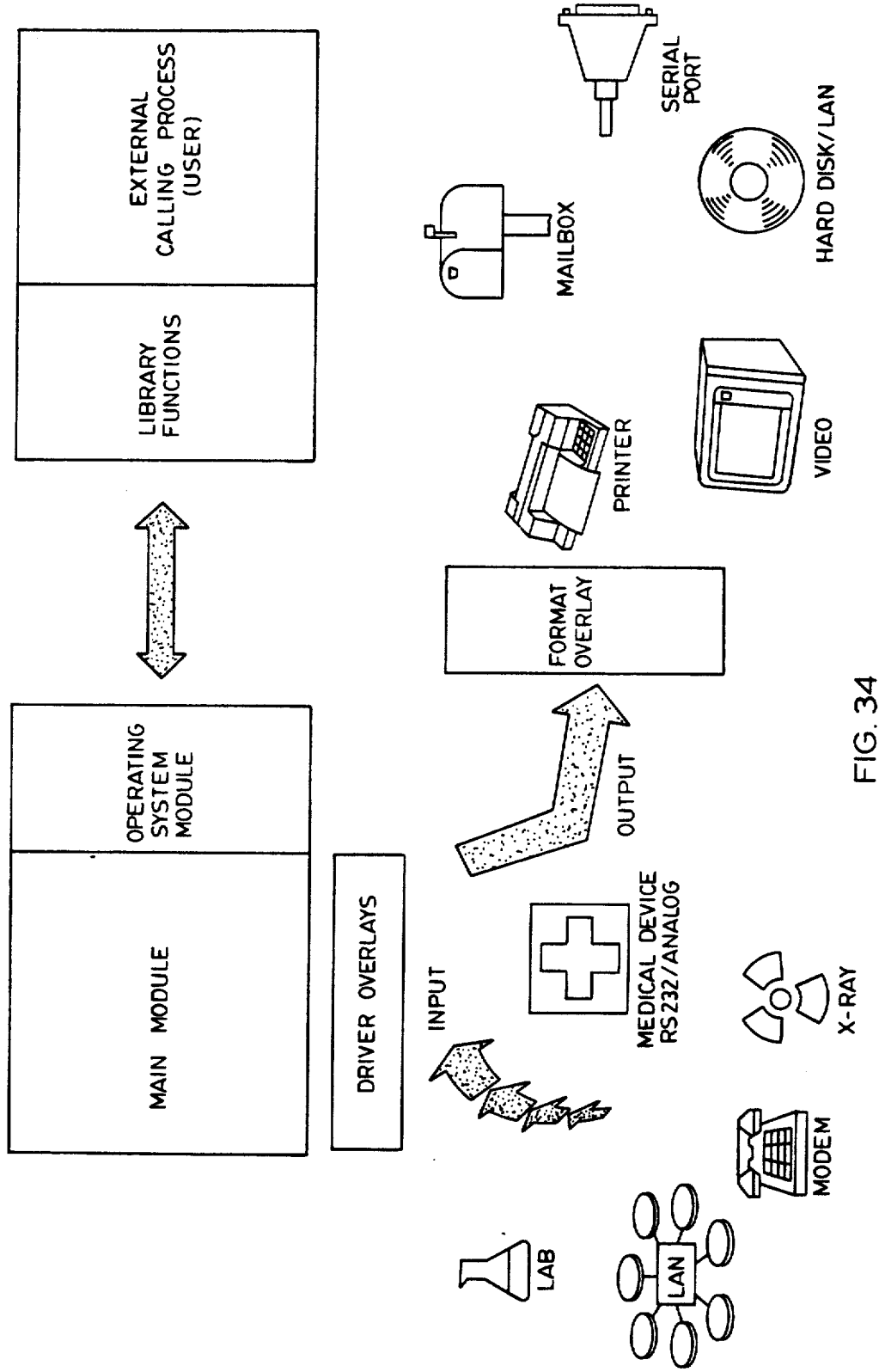
FIG. 34 is a pictorial representation of the various modules which make up the present invention.

As best illustrated by reference to FIG. 34 the method of the present invention is made up of several modules and more particularly a main module, library functions, driver overlays, and format overlays. The main module, which is made up of various steps which are shown in FIGS. 1 through 33 is written in assembly language and is operable to deal with communications, interpretation of user's requests from the external process, the loading and calling of driver overlays, the polling of devices, and the formatting of data and its output to a predetermined destination. In addition to the foregoing, an operating system module is provided and which is operable to permit the main module to operate with various operating systems which are commercially available and which are well-known in the art.

The library functions, and which are contained in a user's library, is an independent program, separate from the main module and which is used by the external process, and which includes the functions which permit the external process to gain access to the main module.

More particularly, the library functions provide a means for internally transforming a user demand and sending it to the main module described above. This library function is completely dependent on the operating system environment while in use. At linking time, the appropriate library is chosen for the operating system in question and one skilled in the art can readily construct a library of their own choice.

The present method includes drivers and driver overlays or skeletons and which will be discussed in greater detail hereinafter. However, it should be understood that the term drivers, when used in this context, means discrete pieces of software that decode the information coming from any device, local area network, or modem. These are separate executable programs which are resident on the hard disk of the computer. Those skilled in the art will readily recognize that drivers can be written in high level languages or in assembly language. In this regard there are several different types of drivers. More particularly, and as discussed hereinafter in greater detail, the drivers employed with the present invention may include serial or analog drivers which include two discrete parts. The first discrete part of a particular device which includes a driver, is the communication setting for the device, that is, the request strings, baud rates, parity, numbers of steps etc. The second discrete element of a driver are the instructions necessary for the decoding of the answer of the sensor being polled. In the case of an analog driver, the first discrete part discussed above is normally replaced by calibration values. Further, and in the case of a local area network driver, a LAN driver can be of three types. The driver can be of a type which retrieves data from a network server, in this case the driver knows the particular path for the data, as well as the instructions to decode it. Further the LAN driver can also emulate tasks, and can read data from a mainframe computer. Thereafter, the LAN can retrieve the data from a network server as noted above. Further, a LAN driver can operate, as described above, but may be further rendered operable to request data from a modem.

Specific output drivers which may be employed with the present invention include two discrete types, that is (1) a driver which can format an answer which is coming from a sensor or device in a user defined format; and (2) a driver which decides where an output is directed, that is, to a printer, serial port output, hard disk, mailbox, etc.

The method of the present invention is operable to store a library of drivers which allows it to communicate with a wide variety of existing medical devices and other diagnostic equipment. Further driver skeletons which may be written in C language and/or in assembly language are provided, and which permit a hospital technician or a programmer to write a proper interface between the main module and any new medical monitoring device which may not be resident in the library of drivers provided. The present invention provides a convenient means whereby, with as little as ten lines of code, an inexperienced programmer can add a driver to the main module library. In this regard, an example of a driver skeleton including the lines of code necessary to enter same are provided, in the example, which will be discussed in greater detail hereinafter.

As should be understood the main module of the present invention and which is illustrated in detail in FIGS. 1-33 is an object oriented system. In this regard the objects are of several types. These include input-/output objects, timer objects, keyboard objects and an object queue. As best seen by reference to Figs. 2 and 34 the communications between the main module and an external calling process or calling task, such as a user [not shown] are achieved through mailboxes. As should be understood, however, the external calling process is a separate executable program which is operable to interface with the main module through the mailboxes and such external calling process programs are commercially available. Examples of such programs are the programs entitled "Atlantis", "Sensor", and "Helena" and which are commercially available through the HMP Corporation of Delaware. However it should be understood that any number of different external process programs may be developed and which are operable to gain access to the main module through the mailboxes. This, of course, permits a user to customize the present invention to provide various functions not described herein. In the present invention however, and when a user issues an external process request or call to the main module, the answer from the main module is returned to the library function issuing the call. Further the main module may respond, on some occasions, through software interrupts thereby preventing the calling task from waiting in loops until an answer is ready. With regard to the timer objects it should be understood that any polling of a sensor device, and which is repetitive, by nature, is associated with a first timer object. Further, and when an answer is expected, a second timer object is automatically activated and which informs the main module when it is suppose to begin decoding the answer returned from the sensor device. Also, and with respect to the keyboard objects, if an operator has a need to know the internal state of the main module, a series of menus and displays are provided which illustrate the actual state of same. Further, the keyboard objects transfer information between the end user and the main module. Finally, and as best understood by reference to FIG. 2 an object queue loop permits the main module to handle with utmost efficiency the different objects described above.

As discussed above, the main module is an interrupt driven software engine. As should be understood this means that any serial communications are hardware interrupt driven. Further, and when a user, including a process or task, requests data from a device or sensor through a specific serial port, the associated hardware interrupt is actuated. Further, the main module polls, if necessary, the device during, or in response to, the first timer object, and sets a delay, or second timer object, for obtaining an answer. Upon receiving this answer it is directly stored into a buffer by code which is executed by the actuated hardware interrupt. In addition to the foregoing, and when the delay timer is off, the main module reads the answer and calls the proper driver for the decoding of the string.

There are a multiplicity of different kinds of messages that a user, including a process or calling task, can transmit to the main module, these include messages which relate to the handling of communication messages, the request for data messages, and the request for specific output messages. Further, a user, that desires to communicate with the main module shall, open communications with the main module by way of a "handle", that is, a communications identification for all their future communications. Furthermore, the user must furnish to the main module an address of the routine for reception of the data. At the end of a session, a message can clear all handles and terminate communications with a calling process or task. Messages may be of various types including a first type, which is used to request data from a specific device on a given serial port, a second type, which carries the name of a local area network driver to be loaded and which is to be operated by the main module, and a third type, which deals with burst messages which are to be read from a server or distant device.

As earlier discussed the main module is operable to provide a means whereby a user can request that a specific format be applied to the data information supplied by the sensor. In this regard, a special message provides to the main module the name of the driver that formats the data in the defined way. Further, a second message expresses the desire of the user to have the output sent to a specific predetermined destination such as a mailbox, serial port, a printer, a file on a hard disk or to a video monitor as conditions warrant. As earlier discussed the main module includes an object queue loop which provides a first in/first out handling of all requests for data information.

Figure 1:
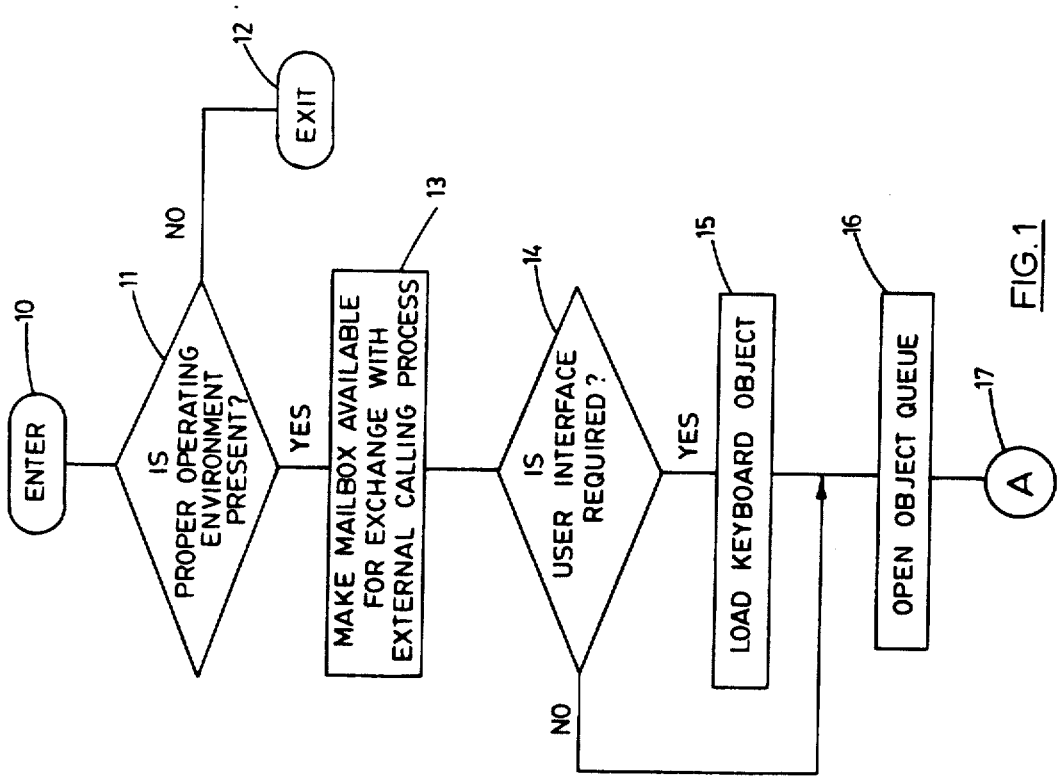
FIG. 1 sets forth in detail the operation of loading the main module of the present invention into a personal computer including opening the object queue.
Figure 8:
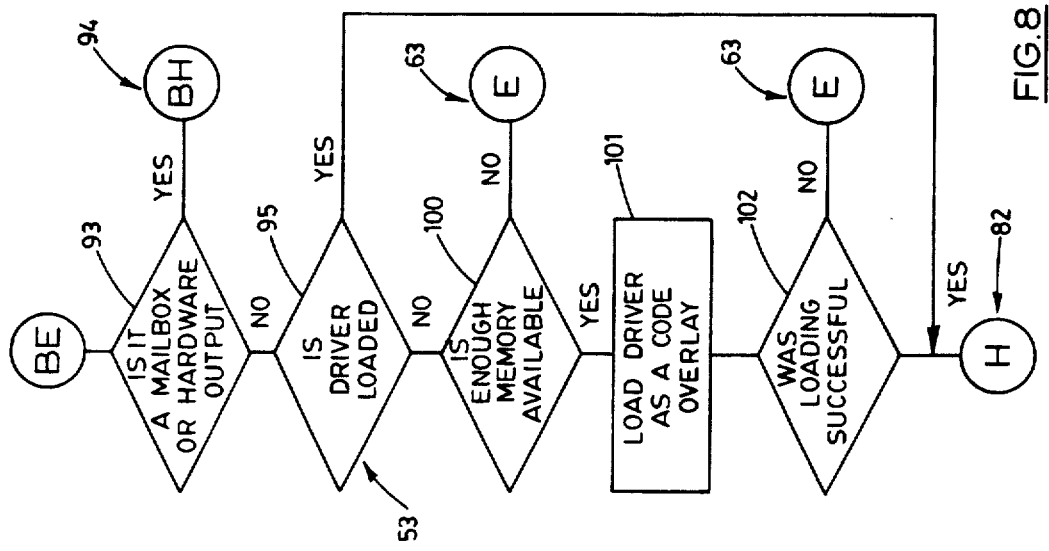
FIG. 8 sets forth in greater detail the mailbox object process shown in FIG. 3.
Figure 7:
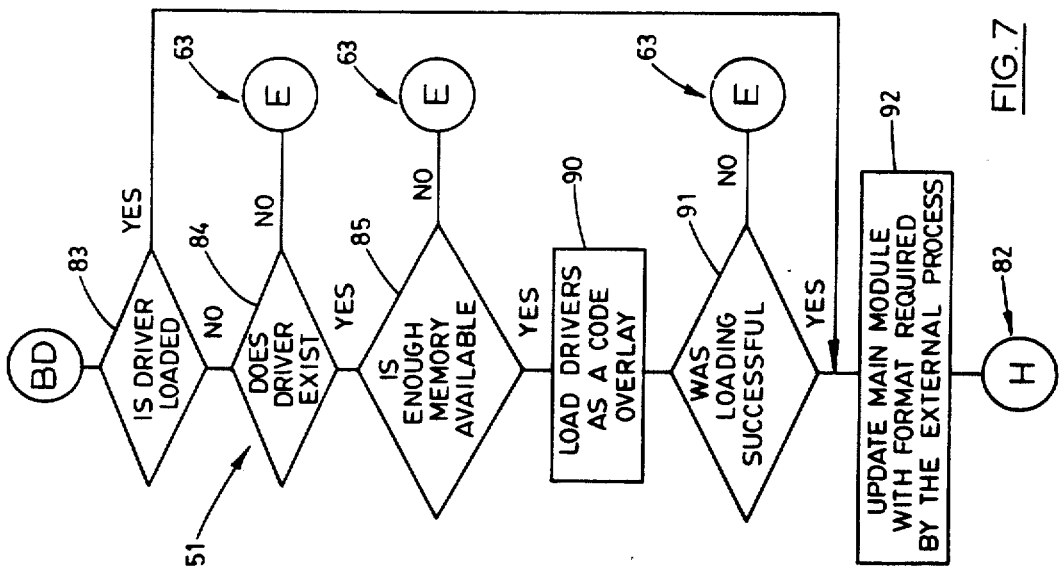
FIG. 7 sets forth in greater detail the mailbox object process shown in FIG. 3.

As best illustrated by reference to FIG. 1 the method of the present invention is loaded into a personal computer, which is not shown, and an operator initiates the present invention at the step labeled "enter" and which is generally indicated by the numeral 10. Upon executing the enter command, the present invention is operable to determine whether a proper operating environment is present 11. If a proper operating environment is absent, the program will exit 12 and will give an appropriate message to the operator. However, in the alternative, and if the proper operating environment is present, the present method makes a mailbox available for exchange with the external calling process 13 which may include such software programs as "Atlantis", "Sensor" and "Helena" and which were discussed above. The method next determines whether a user interface is required 14. If a user interface is required the system is operable to load a keyboard object 15. Upon loading the keyboard object the present method is operable to open the object queue loop 17 and which is set forth in greater detail in subroutine A. Further, and if the user interface is not required the present method is operable to return to the object queue loop which is illustrated in subroutine A in FIG. 2.

The object queue loop 17 and which is best illustrated by reference to FIG. 2, is operable to read the object queue 21 and determine if the object is a mailbox object 22. If it is a mailbox object 22, the object queue is operable to direct the request for data to subroutine B and which is generally indicated by the numeral 23. However, and if the request for information is not of the mailbox type, the object queue loop determines whether the object is a timer object 24. If it is a timer object, then in that event the object queue loop directs the request for information to subroutine C, and which is indicated by the numeral 25. Moreover, and if the object is not a timer object 24, the object queue loop determines whether the object type is a keyboard object 30. If it is a keyboard object, then, in that event, the information is directed to subroutine D and which is generally indicated by the numeral 31. As earlier discussed, the object queue loop is adapted to process the information received from the external process request and then transmit that information to the appropriate subroutine 23, 25, or 31 as appropriate. The object queue loop is the only loop in the present invention and is operable to handle all external process requests on a first in first out basis.

As best illustrated by reference to FIG. 3 subroutine B 23 is operable to process an external process request which has been determined by the object queue loop to be a mailbox object. In this regard subroutine B which may be from time to time referred to as a mailbox object process, determines whether the message received is initiating communication 40. If indeed the external message is initiating communications with the mailbox then, in that event, the message is diverted to subroutine BA, and which is generally indicated by the numeral 41. If the message from the external process is not initiating communication with the mailbox then subroutine B determines whether it is a message from an external process which is loading a driver. If it is, then in that event, the message is diverted to subroutine BB and which is generally indicated by the numeral 43. If the message from the external process is not loading a driver, subroutine B next determines whether it is a message initiating the transmission of data 44. If this is the case then, in that event, the message is diverted to subroutine BC and which is indicated by the numeral 45. If the message does not initiate the transmission of data, then subroutine B next determines whether it is a message for a special format 50. If this is indeed the case then in that event the message is diverted to subroutine BD and which is generally indicated by the numeral 51. Further, and if the message does not request a special format then, in that event, subroutine B determines whether it is a message for a special output 52. If so, then the message is diverted to subroutine BE and which is generally indicated by the numeral 53. In the alternative, and if the message is not a message for a special output, then, in that event, subroutine B determines if it is a message stopping all communications 54. If so, then the message is directed to subroutine BF 55. If not, subroutine B determines if it is a message for stopping communications with just one driver 60. If so, then in that event, it is directed to subroutine BG and which is generally indicated by the numeral 61. If it is none of these messages then, in that event, subroutine B returns to the object queue loop and which is generally indicated by the numeral 17 in FIG. 2.

Subroutine BA, and which is generally indicated by the numeral 41 is best illustrated by reference to FIG. 4. As earlier discussed, and in response to an external process request which has been identified as a mailbox object type 22 and which has been diverted to subroutine B 23 and wherein the message has been determined by subroutine B to be initiating communications 40, subroutine BA is operable to first determine if the external process request is already known 62. If the external process is known, then, in that event the message is directed to subroutine E, and which is generally indicated by the numeral 63 and which is best illustrated by reference to FIG. 15. As shown therein, subroutine E generates an error message 162 to the end user. If the external process is not known, then, in that event, subroutine BA determines if the program is free enough to handle the external process 64. If not, subroutine BA is operable to divert the request for data to subroutine E 63 and thereby generate an error message to the end user. If the process is able to handle the external process, then, in that event, subroutine BA is operable to open a handle 70. As earlier discussed a handle is an identification tag, of sorts. Subroutine BA stores the identification or handle in memory. The step of opening the handle and storing the identification of the external process is indicated by the numeral 70. Upon completing the step of identifying the external process, subroutine BA sends an "okay" message and the identification "handle" to the external process through the mailbox 71. Upon completion of this task, subroutine BA returns to the object queue loop and which is generally indicated by the numeral 17.

As earlier discussed the mailbox object process, and more particularly subroutine B, and which is generally indicated by the numeral 23 in FIG. 3, is operable to determine if an external process message is loading a driver 42. If the external process is loading a driver, the message is diverted to subroutine BB and which is generally indicated by the numeral 43 in FIG. 5. As shown therein, subroutine BB is initially operable to determine if the driver type is a device driver 72. If this is not the case, then, in that event, the message is diverted to subroutine F and which is generally indicated by the numeral 73. If the message is for a device type driver, then, in that event, subroutine B determines if the driver is loaded 74. If the driver is not loaded, then, in that event, the message is directed onto subroutine G 75 and which will be discussed in greater detail hereinafter. If the driver is loaded, then, in that event, subroutine B is operable to decode the variables requested by the external process 76, update the driver overlay with the variables requested by the external process 80, and update the main module with the variables requested by the external process 81. Upon completion of this last task subroutine BB, 43 returns to subroutine H 82 and which will be discussed in greater detail hereinafter.

The mailbox object process and which is generally indicated by the numeral 23, is operable to determine if a message from the external process was initiating the transmission of data 44. If this answer is in the affirmative then, in that event, the message is diverted to subroutine BC and which is generally indicated by the numeral 45 in FIG. 6. As shown therein subroutine BC is operable to initiate the transfer of data from the main module to the external process 83 and then return to subroutine H and which is generally indicated by the numeral 82.

The mailbox object process and more particularly subroutine B 23 is operable to determine if a message from an external process is requesting a special format 50. If this answer is in the affirmative, then, in that event, the message is diverted to subroutine BD and which is generally indicated by the numeral 51 in FIG. 7. As shown therein, subroutine BD is operable to determine if the driver is loaded 83. If the response to same is in the affirmative, then, in that event, subroutine BD is adapted to update the main module with the format required by the external process 92 and return to subroutine H and which is generally indicated by the numeral 82. However, and if the driver is not loaded, subroutine BD is operable to next determine if the driver exists 84. If the driver does not exist, an error message is generated by means of subroutine E and which is generally indicated by the numeral 63. In the alternative, and if the driver does exist subroutine BD next determines if enough memory is available for processing the request 85. If a response to same is in the negative, then, in that event, subroutine E is executed and which is generally indicated by the numeral 63. In the alternative, and if sufficient memory is available to process the request 85 then, in that event, subroutine BD is operable to load the driver as a code overlay 90.

Subroutine BD then determines whether loading was successful 91. If not, an error message through subroutine E 63 is executed. In the alternative and if loading was successful, then, in that event, subroutine BD is operable to update the main module with the format required by the external process 92 and then return to subroutine H 82, as earlier discussed.

The mailbox object process 23 is operable, as earlier discussed, to determine if a message received from an external process is a message for a special output 52. If this answer is in the affirmative, then, in that event, the message from the external process is diverted to subroutine BE and which is generally indicated by the numeral 53 in FIG. 8. As shown therein, subroutine BE is operable to first determine if the message from the external process is a mailbox or hardware output 93. If the answer is in the affirmative, then, in that event, the message is diverted to subroutine BH and which is generally indicated by the numeral 94. In the alternative and if the answer is a negative response, then, in that event, subroutine BE next determines if the driver is loaded. If the driver is loaded, then the subroutine is operable to determine if loading was successful 102. If not, an error message through subroutine E 63 is generated. If loading, was successful, then, in that event, the message is transmitted to subroutine H, and which is generally indicated by the numeral 82. If the driver is not loaded then subroutine B is operable to thereafter determine if enough memory is available for processing the request 100. If sufficient memory is not available, an error message by means of subroutine E 63 is provided. If indeed sufficient memory is available, subroutine BE loads the driver as a code overlay 101 and thereafter determines whether loading was successful 102. If not, subroutine E 63 is executed thereby generating an error message. If loading was successful, then, in that event, the message is transmitted to subroutine H and which is generally indicated by the numeral 82.

Subroutine BH and which is generally indicated by the numeral 94 is operable, upon receiving a message indicating that a message is a mailbox or hardware output 93 from subroutine BE 53, to execute and store the parameters for redirecting all data of the external process 103 and return the information to subroutine H and which is generally indicated by the numeral 82.

Subroutine BF and which is generally indicated by the numeral 55 is best illustrated by reference to FIG. 10, and is operable to receive a message from the external calling process which is directing the present invention to stop all communications 54. In this regard, subroutine BF is adapted to reset all parameters concerning the external process and free its handle 104 and thereafter determine if each of the drivers previously requested by the external process are in use by another external process 105. For the drivers which are in use, nothing occurs. For those drivers not in use then, in that event, subroutine BF is operable to reset the main module for that driver and stop any polling timers 110. Further, and following step 110, subroutine BF is adapted to determine if the driver is a device driver 111. If not, the information is returned to subroutine H 82. However, and if it is a device driver, then, in that event, subroutine BF executes a command to free a serial port 112 as best seen by reference to FIG. 10

As earlier discussed, the mailbox object process and which is generally indicated by the numeral 23 in FIG. 3 is operable to determine if the message from the external process is stopping communications with one driver 60. If the answer to the message is in the affirmative, then, in that event, the information is sent to subroutine BG and which is generally indicated by the numeral 61 in FIG. 11. As shown therein, subroutine BG is operable upon receiving the information, to update the main module parameters for the particular process 113 and thereafter inquire whether the driver is in use by another process 114. If this determination is in the affirmative, the information is directed to subroutine H 82. If the answer is in the negative, then, subroutine BG is operable to reset the main module parameters for the driver effected and stop polling 115. Further, subroutine BG is operable to determine if the driver is a device 116. If the answer is in the negative, then, in that event, subroutine BG is operable to direct the information to subroutine H 82. If the answer is in the affirmative, subroutine BG frees up a serial port 117 and then proceeds to direct the information to subroutine H. This is best understood by a study of FIG. 11.

FIG. 12 illustrates subroutine G 75 and which receives information following a determination in subroutine BB, and which is generally indicated by the numeral 43, that a driver is not loaded to memory 74. Upon receiving information ,subroutine G determines if the requested port is free 120. If the answer is in the negative then, in that event, an error message is generated by means of subroutine E 63. If the answer is in the affirmative, subroutine G next determines if the driver exists 121. If not, then, in that event, subroutine E is utilized and an error message is generated. In the alternative, and if the driver does exist, subroutine G determines if enough memory is available to process the information 122. If sufficient memory is not available an error message is generated by means of subroutine E. Alternatively and if the answer is in the affirmative, subroutine G is operable to load the driver as a code overlay 123 and determine if loading was successful by means of step 124. If loading was not successful then, in that event, subroutine E 63 generates an error message. However, and if loading was successful, subroutine G sequentially reads the driver communication settings 125, decodes the variables requested by the external process 130, updates the main module with the variables requested by the external process 131, sets the ports and hooks the corresponding IRQ of the hardware, if necessary, 132 and creates a polling timer object associated with the device 133 Further and upon the successful creation of a polling timer 133, subroutine G determines if the device is pollable 134. If not, the information is passed to subroutine H. However and if the device is pollable, then, in that event, subroutine G creates a delay timer object associated with the device 135 and then sends a request to the device 140 and starts a delay timer which is flagged to a handshake 141. Following the handshake, which initiates communication, subroutine G returns to the object queue loop 17 as best illustrated by reference to FIG. 2.

As earlier discussed the mailbox object process 23 is operable to determine if a message received from an external process is loading a driver 42. Further and if the driver is not a device driver 72 as determined by subroutine BB 43 then, in that event, subroutine F is operable to process the information and which is generally indicated by the numeral 73 in FIG. 13. Initially subroutine F determines whether the driver is loaded 142. If subroutine F determines that the driver is not loaded, then, in that event, it determines whether the driver exists in memory 143. If the driver does not exist in memory, then, an error message by means of subroutine E 63 is generated. However, and if the driver does not exist in memory, subroutine F subsequently determines if enough memory is available to handle the external process request 144. A negative determination of this query generates an error message by means of subroutine E 63. However, and if enough memory is available, then, in that event, subroutine F loads the driver as a code overlay 145 and thereafter determines whether loading was successful 150. Failure to load successfully generates an error message by means of subroutine E 63. Successful loading results in subroutine F thereafter determining if the driver under consideration is importing data 151. If not, the information is directed to subroutine K and which is generally indicated by the numeral 152 in FIG. 14. However, and if the driver is for importing data, then, in that event, subroutine F decodes the variables requested by the external process 153, updates the driver overlay with the variables requested by the external process 154, and updates the main module with the variables requested by the external process 155. Following the last step, subroutine F returns the information to subroutine J and which is indicated by the numeral 156.

Subroutine K and which is generally indicated by the numeral 152 in FIG. 14 is operable to process information from subroutine F following a determination that a driver is not being utilized for importing data 151. In this regard, subroutine K is operable to determine if the message is a timer object dependent driver 160. Following an affirmative determination, subroutine K is operable to transmit the information to subroutine J and which is generally indicated by the numeral 156. A negative determination causes subroutine K to call the appropriate code overlay 161 and then transmit the information to subroutine H and which is generally indicated by the numeral 82. Further, and as best illustrated by reference to FIG. 15, subroutine E is operable to generate an error message at various points in the present method. As best illustrated by reference to FIG. 16, subroutine H is operable upon receiving information to notify the external process 163 of an okay status via a mailbox and then return to the object queue loops 17 and which was earlier discussed in greater detail. Further, and as best illustrated by reference to FIG. 17, subroutine J and which is generally indicated by the numeral 156, upon receiving information, is operable to create a polling timer associated with the driver 164 and then return the information to subroutine H and which is indicated by the numeral 82 in FIG. 16.

Subroutine C and which is generally indicated by the numeral 25 illustrates, in general, the object timer process and which is generally indicated by the numeral 25 in FIG. 2. The object timer process C is operable to initially determine whether the external process request is a polling timer request 170. If this answer is in the negative then, in that event, the external process request is directed to subroutine L and which is generally indicated by the numeral 171. Subroutine L will be discussed in greater detail hereinafter. Further, and if the message is a polling timer request, then, in that event, subroutine C is operable to restart the polling timer 172 and determine if the corresponding driver is a pollable one 173. As should be understood, some drivers are not pollable. If the driver is not pollable then, in that event, the information is directed to subroutine LB and which is generally indicated by the numeral 174. In the alternative, and following a determination that the driver is pollable, subroutine C next determines if the driver is a device driver 175. If the device is not a device driver, then, in that event, the information is directed to subroutine M, and which is generally indicated by the numeral 176 Further, and if the device is a device driver, subroutine C sends a first polling request to the proper port 177 and then starts the associated delay timer 178. Following completion of the start the associated delay timer, 178, subroutine C returns to the object queue loop and which is generally indicated by the numeral 17 in FIG. 2.

Figure 18:
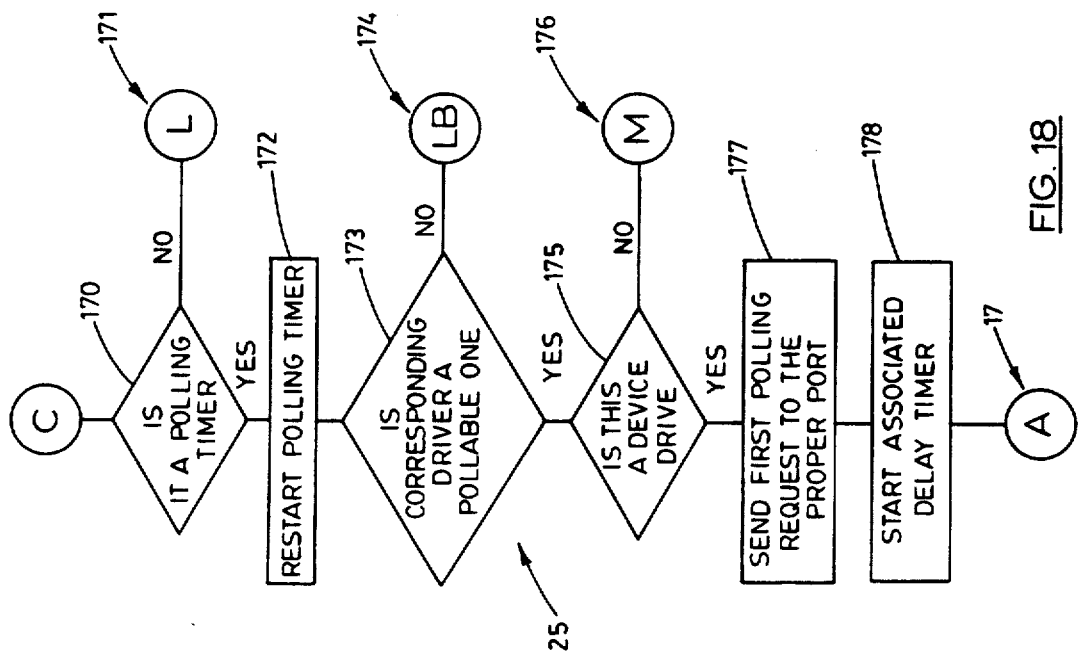
FIG. 18 sets forth in further detail the object timer process of the present invention and more particularly the operation of the object timer process and which is shown in FIG. 2.
Figure 17:
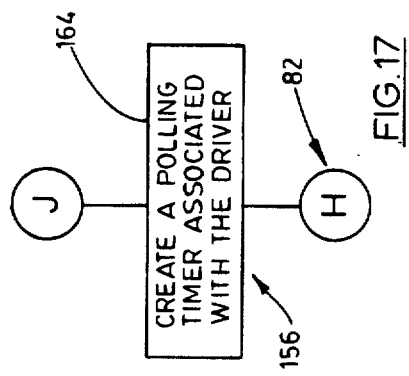
FIG. 17 sets forth in further detail the mailbox object process and more particularly the operation for creating a polling timer associated with the driver of the present invention and which is shown in FIG. 14.
Figure 15:
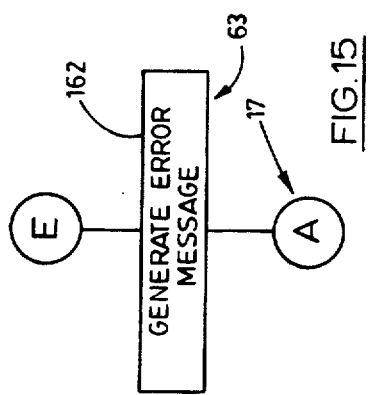
FIG. 15 shows in greater detail the mailbox object process and more particularly the operation of generating an error message and which is shown in FIG. 4.
Figure 16:
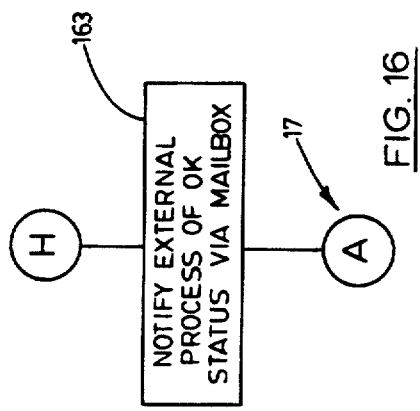
FIG. 16 shows in greater detail the mailbox object process and more particularly the operation of notifying an external process of the status of the system by way of a mailbox and which is shown in FIG. 14.

FIG. 19 illustrates subroutine M 176 and which receives information from the object timer process and which is generally indicated by the numeral 25 in FIG. 18. Subroutine M receives information from subroutine C and more particularly the information that the device under consideration is not a device driver 175. Following receipt of this information, subroutine M initially determines whether the non-device driver is for importing data 80 and if it is not, then, in that event, the information is directed onto subroutine 0, and which is generally indicated by the numeral 181. If the device is a non-device driver, then, in that event, subroutine M calls the proper code overlay 182 and directs the information onto subroutine RO, and which will be discussed hereinafter as numeral 183.

Subroutine 0, and which is generally indicated by the numeral 181, in FIG. 20, is operable to determine, following a negative determination that the non-device driver is for importing data 180 to call an appropriate code overlay 184 and then determine if the message being received is a burst message 185. If the message is a burst message, then, in that event, the information is directed to a video screen 186. The subroutine then returns to the object queue loop 17. However, and in the alternative, if the information is not a burst message, then, in that event, subroutine 0 determines if the message is an operating system call request 190. If indeed, it is an operating system call request, then, in that event, subroutine o executes the system call and inquires if there is an output to redirect. If indeed there is an output to redirect, then, in that event, the information is directed to subroutine RO and which is generally indicated by the numeral 183. However, and if there is no output to redirect, subroutine 0 returns to the object queue loop A and which is generally indicated by the numeral 17.

Figure 21:
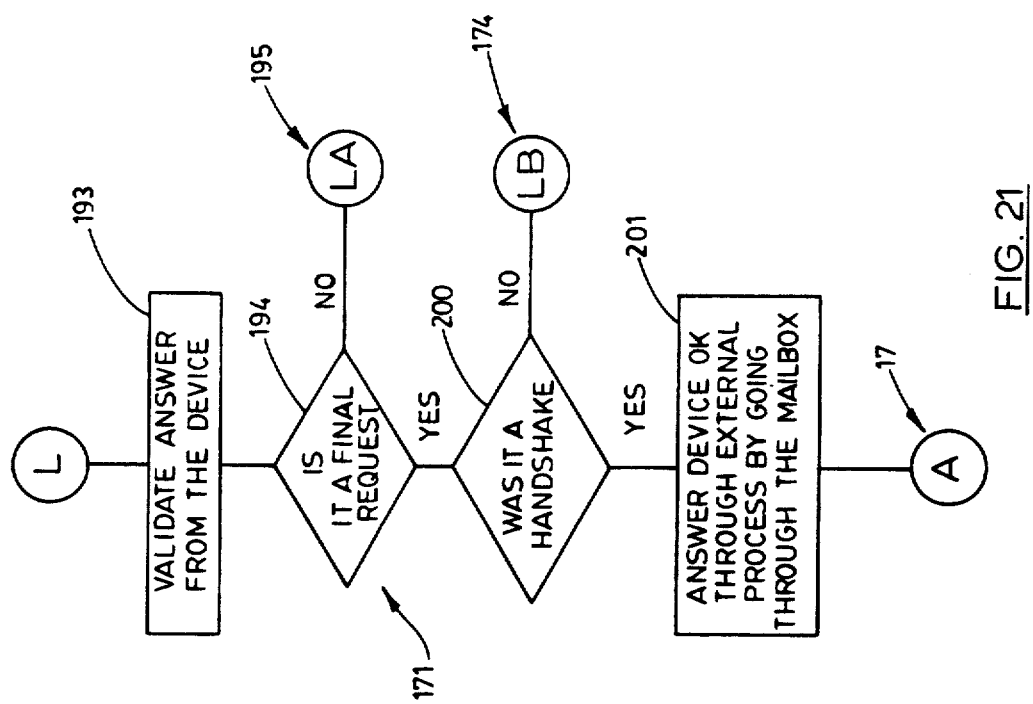
FIG. 21 sets forth in further detail the object timer process of the present invention and more particularly the operation following a determination that a message does not relate to a polling timer and which is shown in FIG. 18.

As best illustrated by reference to FIG. 21, subroutine L, and which is generally indicated by the numeral 171, is operable to receive information from the object timer process 24, and which is generally indicated by the numeral 25 in FIG. 18. Subroutine L is operable, upon receiving information from subroutine C, to validate the answer from the device 193 and determine if it is a final request 194. If it is not a final request 194, then, in that event, the information is transmitted to subroutine LA, and which is generally indicated by the numeral 195 in FIG. 21. If the information received is a final request, then, subroutine L is operable to determine if it was a handshake initiating communications 200. If it was not, then, in that event the information is directed to subroutine LB and which is generally indicated by the numeral 174 in FIG. 22. If, in the alternative, the final request was a handshake initiating communication, then, in that event, subroutine L initiates an answer to the device with an okay through the external process by going through the mailbox 201 and then returns to the object queue loop which is generally indicated by the numeral 17.

Figure 35:
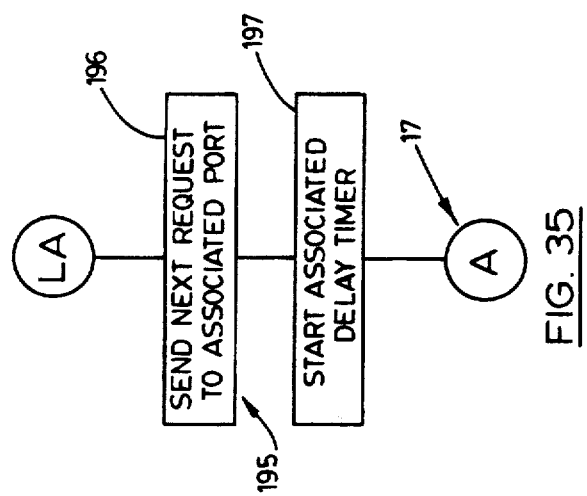
FIG. 35 sets forth in further detail subroutine LA of the present invention.

Subroutine LA and which is generally indicated by the numeral 195 in FIG. 35 is operable, upon receiving information to send the next request for information to an associated port 196, and then start the associated delay timer 197. Subroutine LA then returns to the object queue loop 17.

Figure 22:
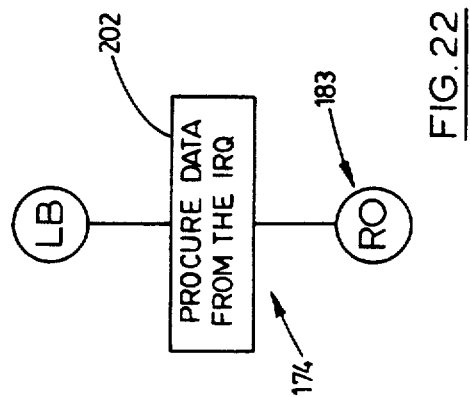
FIG. 22 sets forth in further detail the object timer process of the present invention and more particularly the operation following a determination that a driver is not a pollable one as shown in FIG. 18.

Subroutine LB and which is generally indicated by the numeral 174, in FIG. 22, is operable to receive information from the object timer process and which is generally indicated by the numeral 25 in FIG. 18, and more specifically to receive information regarding whether the corresponding timer is a pollable one as provided at 173. If the driver is not a pollable one, then, in that event, the information is processed through subroutine LB. More specifically, subroutine LB, procures the data from the IRQ of the hardware and then returns to subroutine RO, and which is generally indicated by the numeral 183 and which is illustrated with more particularly in FIG. 32.

Figure 23:
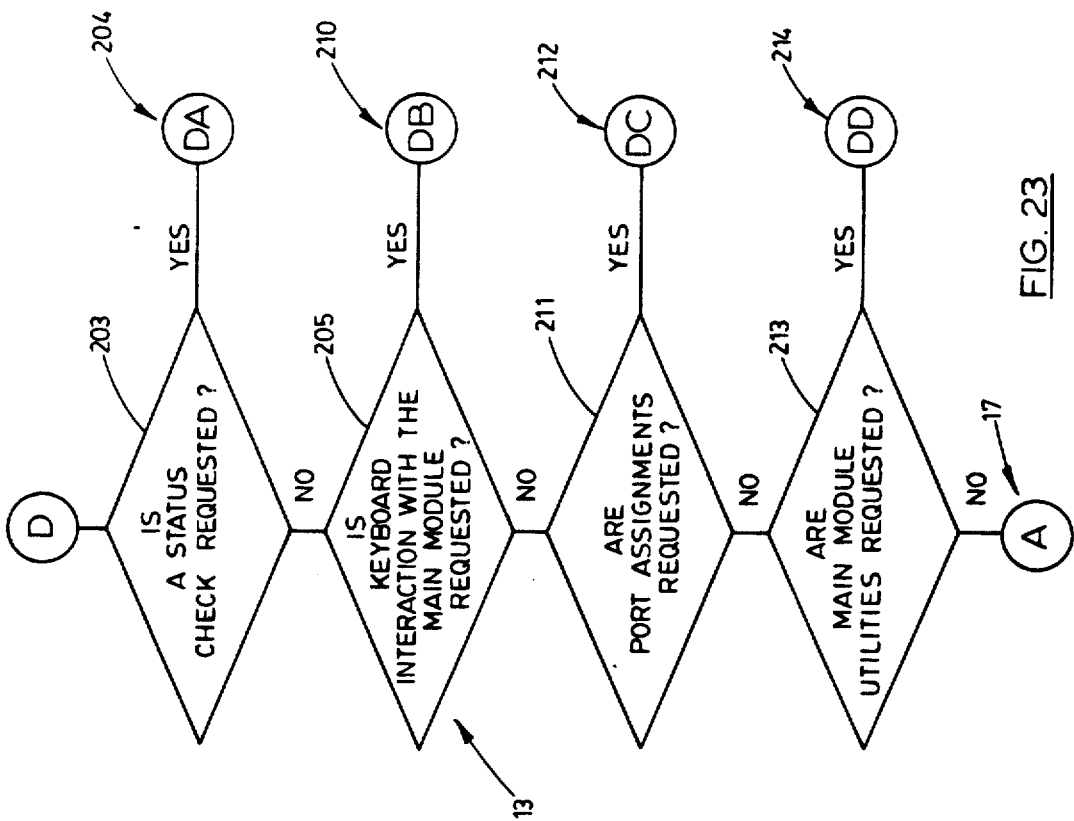
FIG. 23 sets forth in further detail of the keyboard object process shown in FIG. 2.
Figure 33A:
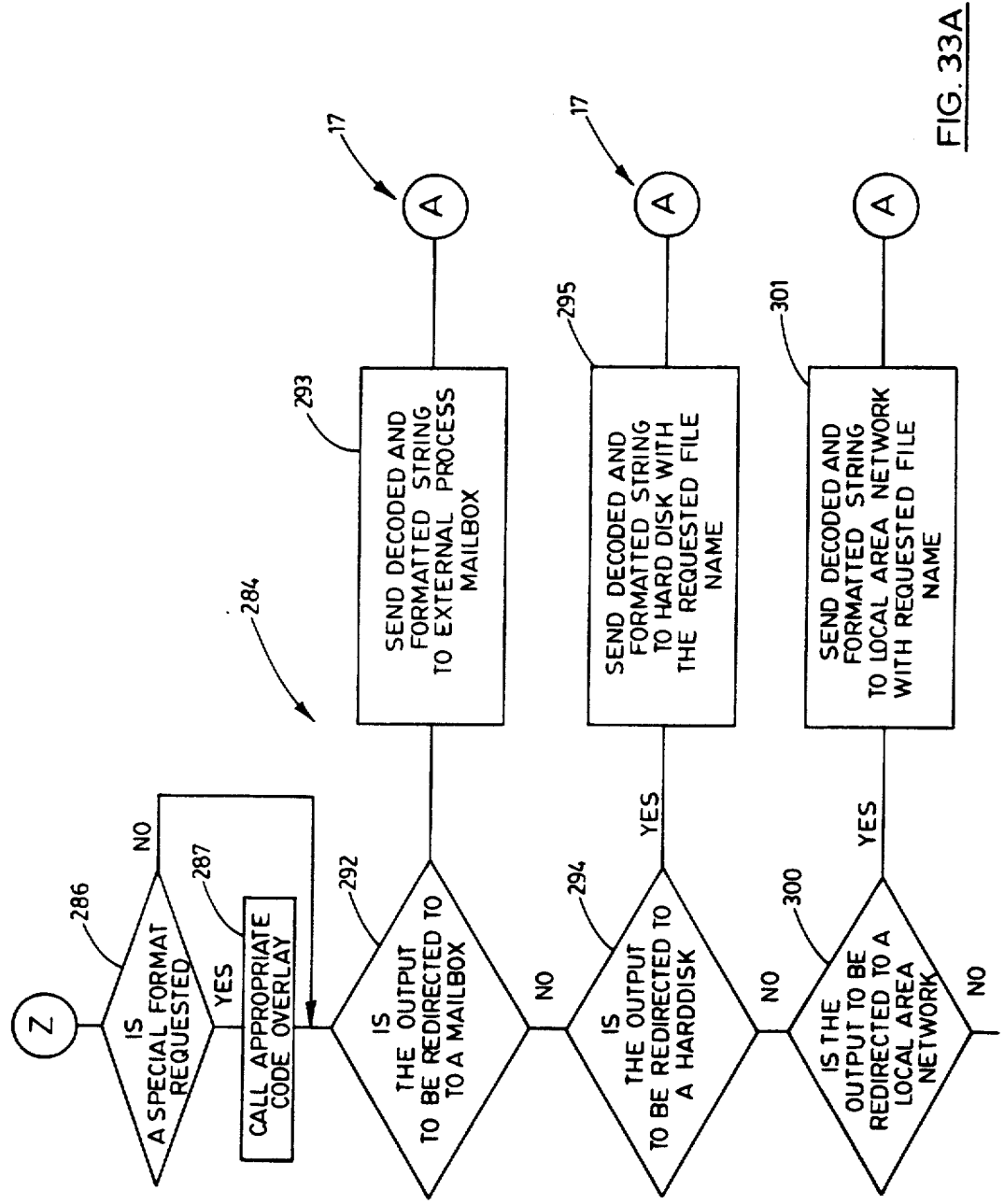
FIGS. 33A and 33B set forth in further detail the keyboard object Process, and more particularly the operation following a determination that a video output has not been requested and which is best illustrated by reference to FIG. 32.
Figure 33B:
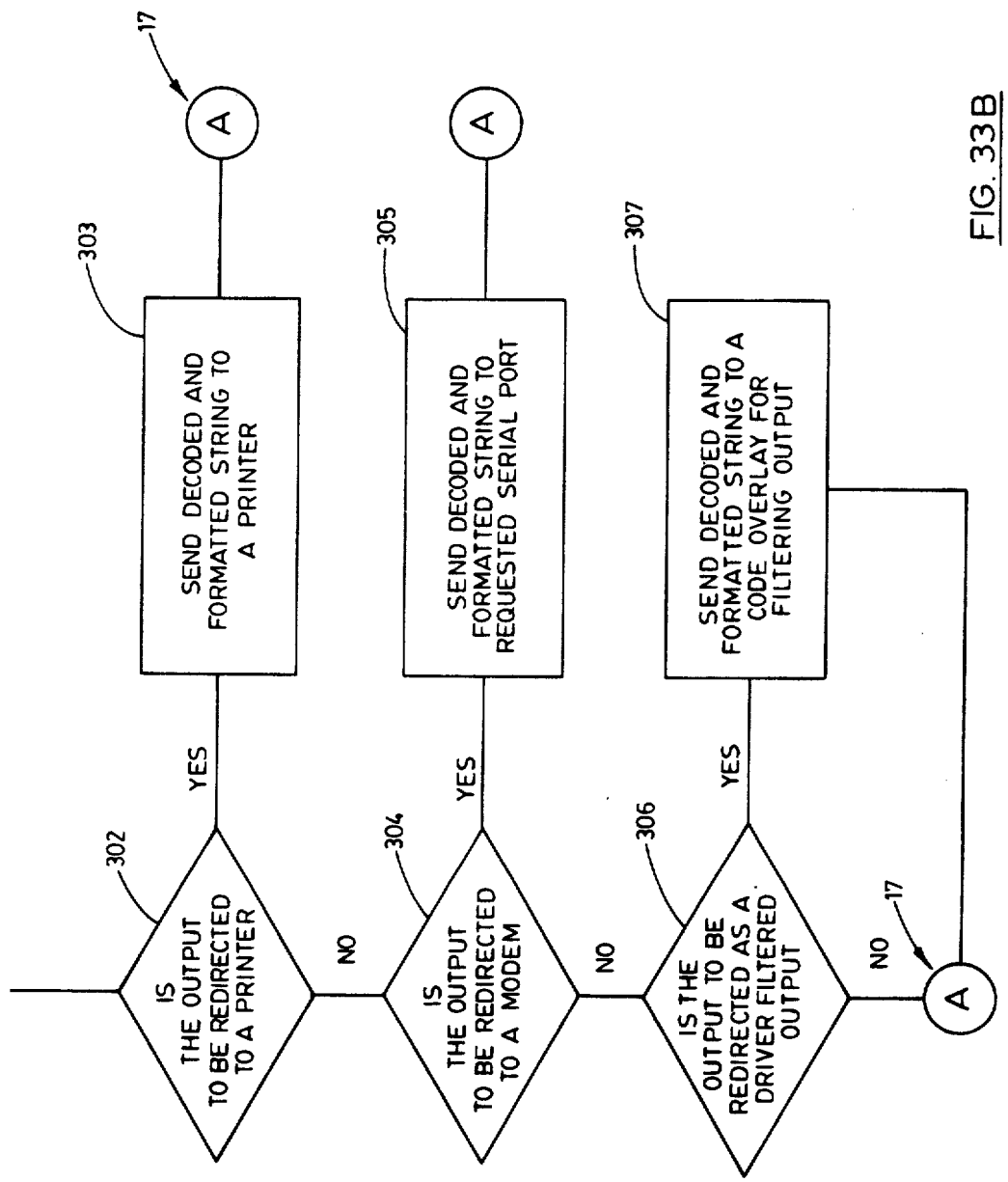
Figure 36:
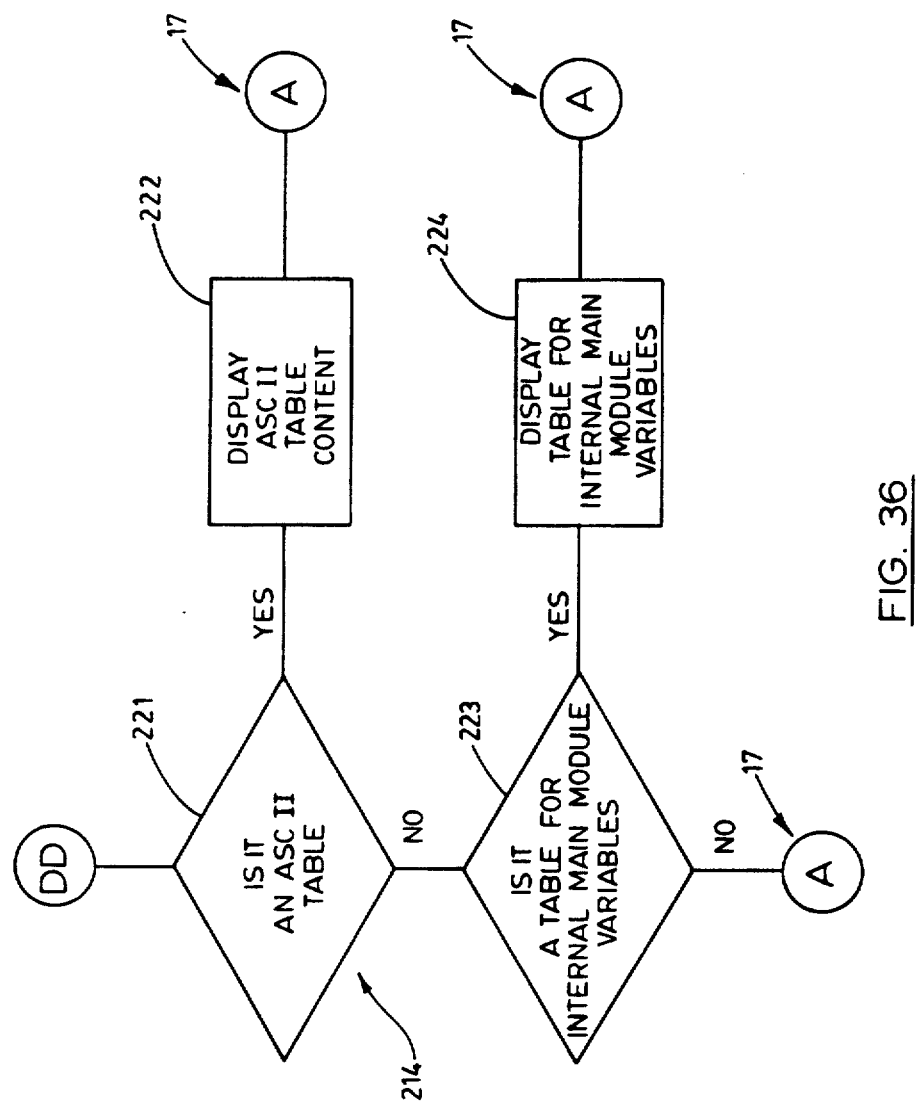
FIG. 36 sets forth in further detail subroutine DD of the present invention.

FIG. 23 illustrates in more detail the keyboard object process and which is generally indicated by the numeral 31 in FIG. 2. Subroutine D is operable initially to determine whether the request from the external process is a status check request 203, and if this is the case, the information is directed to subroutine DA and which is generally indicated by the numeral 204. Further, and if the information from the external process is not a status check request 203, then, in that event, subroutine D is operable to determine if keyboard interaction with a main module is requested 205. If a response to this question is in the affirmative, then, in that event, the information is directed to subroutine DB and which is generally indicated by the numeral 210 in the alternative and if a response is in the negative, then, in that event, subroutine D is operable to determine if port assignments are requested 211. If this is the case, then, in that event, the information is directed onto subroutine DC 212. If port assignments are not requested, then, in that event, subroutine D is operable to determine whether the main module utilities are requested. If the answer is in the affirmative, then, in that event, the information is directed to subroutine DD 214. As should be understood subroutine DD and which is shown in FIG. 36, is operable to determine if an ASCII table is requested 221, or if a main module variable table is requested 223. Upon displaying the requested information 222, and 224, respectively, subroutine DD returns to the object queue loop 17 and which is best illustrated in FIG. 2.

Figure 24:
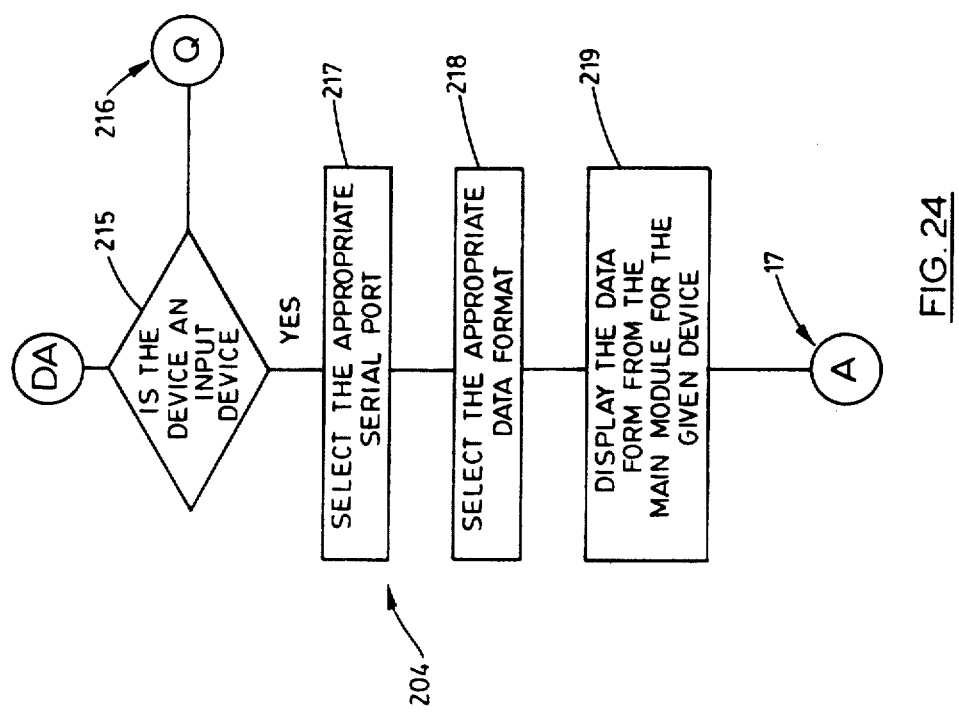
FIG. 24 sets forth in further detail the keyboard object process, and more particularly the operation following an affirmative status check request and which is shown in FIG. 23.

FIG. 24 illustrates subroutine DA, and which is generally indicated by the numeral 204. Subroutine DA is operable to receive the information from the keyboard process request, and which is generally indicated by the numeral 31, in FIG. 23. Subroutine DA is operable, upon receiving the information regarding whether the external process is requesting a status check 203 and thereafter determine if the device is an input device 215. If the device is not an input device, then in that event the information proceeds to subroutine Q and which is generally indicated by the numerals 216. However, and if the device is an input device, then, in that event, subroutine DA is operable to select the appropriate serial port 217 select the appropriate data format 218 and; thereafter display the data form 219 from the main module for the given device 219. Upon completion of the last step of displaying the data, subroutine DA 204 returns to the object queue loop, and which is generally indicated by the numeral 17.

FIG. 25 illustrates subroutine Q, and which receives information from subroutine DA in FIG. 24. Upon a determination that a device is not an input driver, subroutine Q is operable to receive the information, and select the appropriate data format 230 from the main module for the given device 231. Upon completion of the last step, 231, subroutine Q returns to the object queue loop and which is generally indicated by the numeral 17 in FIG. 2.

Subroutine DB and which is generally indicated by the numeral 210, receives information from the keyboard object process and which is generally indicated by the numeral 31 in FIG. 23. Subroutine DB, upon receiving information from the keyboard object process D, is operable to determine if the request is a message for a driver 232. If the request is for a driver, then, in that event, the information is directed to subroutine R and which is generally indicated by the numeral 233. Further, and if the foregoing answer is in the negative, then, in that event, subroutine DB next determines if the request is for a special format 234. If indeed it is, then, in that event, the information is directed onto subroutine S, and which is generally indicated by the numeral 235. In the alternative and if the request is not for a special format, then, subroutine DB determines if it is a request for a special output 240. If so, then, in that event, the information is directed to subroutine T and which is generally indicated by the numeral 241. However, and if the information is not for a special output 240 then, in that event, subroutine DB next determines if it is a request for stopping all communications 242. If the answer to the last query is in the affirmative, then, in that event, the information is directed to subroutine BF, and which is generally indicated by the numeral 55. Alternatively, and if the request does not stop all communications, then in that event, subroutine DB determines if it is a request for stopping communications with only one driver 243. If the request is in the negative, then in that event, subroutine DB returns to the object queue loop, and which is generally indicated by the numeral 17. Alternatively, and if it is a request stopping communications with only one driver, then, in that event, subroutine DB requests which driver communications is to be stopped, and thereafter directs the information to subroutine BG and which is generally indicated by the numeral 61 and which was discussed in detail earlier.

Subroutine R and which is generally indicated by the numeral 233 in FIG. 27 is operable to receive information from subroutine DB and which is indicated by the numeral 210 in FIG. 26. Subroutine R is operable, upon receiving information, to select the serial port or local area network as appropriate 250 and execute a request for the name of the driver (code overlay to be loaded) 251. Upon completion of step 251, subroutine R determines if the information is a driver for imparting variables 252. If indeed it is, then, in that event, subroutine R executes the request for variables 253 and thereafter builds the request in the form of a mailbox request 254. Upon completion of the step 254, subroutine R returns to subroutine BB and which is generally indicated by the numeral 43 and which was discussed in the above paragraphs.

As best illustrated by reference to FIG. 28, subroutine S 235 receives information from subroutine DB and is operable to select the format of the code overlay as appropriate 260 for the message received and thereafter executes a command to build a request in the form of a mailbox request 261. Subroutine DB subsequently returns to subroutine BD 51 as indicated in FIG. 28. In addition to the foregoing, subroutine T, and which is generally indicated by the numeral 241 in FIG. 29, is operable to receive the special output message 240 from subroutine DB 210 and thereafter determines if the output is a mailbox or hardware output 262. If the output is not a mailbox or hardware output, then, in that event, the information is diverted to subroutine TA and which is indicated by the numeral 263 in FIG. 30. If, in the alternative, the output is a mailbox or hardware output, then, in that event, subroutine T is operable to request the parameters of same 264 and then return to the object queue loop, and which is generally indicated by the numeral 17 in FIG. 2.

Subroutine TA, and which is indicated by the numeral 263 in FIG. 30, is operable to receive information from subroutine T in FIG. 29 and is further operable upon receiving that information to request a driver name 270 and then determine if the driver is loaded 271. If the driver is loaded, then in that event, subroutine TA is operable to update the main module with the format requested by the external process 276 and then return to subroutine H 82. Alternatively, and if the driver is not loaded, subroutine TA is operable to determine if the driver exists, and if the answer is in the negative, then in that event it generates an error message by means of subroutine E 63. However, if the driver does exist, subroutine TA next determines if sufficient memory is available to handle the request 273, and if not, an error message is generated by means of subroutine E 63. Alternatively, and if sufficient memory is available, then, in that event, subroutine TA loads the driver as a code overlay 274, and determines if loading was successful by means of step 275. An error message is generated in the event that loading was not successful 63. If loading was successful, then, in that event, an update of the main module proceeds with the format requested by the external process 276 and thereafter subroutine TA returns to subroutine H, and which is generally indicated by the numeral 82.

As best illustrated by reference to FIG. 31, subroutine DC, and which is indicated by the numeral 212 in FIG. 23, receives information from the keyboard object process 31 and is operable, upon receiving the information, to sequentially select the serial port 280 requested, enter the base address and IRQ of the information 281, and then save the new settings 282 as appropriate. Upon completing the last step 282, subroutine DC returns to the object queue loop A, and which is generally indicated by the numeral 17 in FIG. 2.

As best illustrated by reference to FIG. 32, subroutine RO is adapted to receive information from subroutine M (FIG. 19) and then determines whether the information is an output on video 283. If the request for the information is not an output on video, then, in that event, the information is directed to subroutine Z, and which is generally indicated by the numeral 284 in FIG. 32. However, and if it is a video output request, then in that event, subroutine RO determines whether the information is a special format request 285. In the event that the information received is a special format request, then, in that case, subroutine RO executes a call appropriate for the format code overlay 290 and thereafter calls the main module routine for displaying the results 291, as appropriate. Upon achieving the last step 291, subroutine Ro returns to the object queue loop A and which is generally indicated by the numeral 17 in FIG. 2.

Subroutine Z, and which is generally indicated by the numeral 284 in FIGS. 3A-B is operable, upon receiving information from subroutine RO, to determine if the request is for a special format 286. If the answer is in the affirmative then, in that event subroutine Z is operable to call the appropriate code overlay 287 and thereafter determine if the output is to be redirected to a mailbox 292. If this determination is in the affirmative, then, in that event, subroutine Z sends the decoded and formatted string to the external process mailbox 293, and then returns to the object queue loop 17. If, in the alternative the determination is negative, then, in that event, subroutine Z next determines whether the output is to be redirected to a hard disk 294. If the determination is affirmative, then, in that event, subroutine Z sends the decoded and formatted string to the hard disk with a requested file name 295 and thereafter returns to the object queue loop, and which is generally indicated by the numeral 17 in FIG. 2. If the information is not to be redirected to a hard disk, subroutine Z next determines if the output is to be redirected to a local area network 300. If the response to this query is in the affirmative, then, in that event, subroutine Z sends the decoded and formatted string to a local area network with the requested file name 301 and then returns to the object queue loop 17. Alternatively, and if the information is not to be redirected to a local area network then, subroutine Z determines if the output is to be redirected to a printer 302. If this last determination is in the affirmative, then, in that event, the decoded and formatted string is sent to a printer 303, and subroutine Z returns to the object queue loop 17 Alternatively, and if the determination to the previous query, is negative, then, subroutine Z determines if the output is to be redirected to a modem. If the information is to be directed to a modem then the decoded and formatted string is transmitted to the requested serial port 305. Similarly and upon transmission to the requested serial port, subroutine Z then returns to the object queue loop 17. Further, and if the information is not to be redirected to a modem, then, in that event subroutine Z next determines if the output is to be redirected as a driver filtered output. If the answer to the previous query is in the affirmative, then, the subroutine sends the decoded and formatted string to a code overlay for filtering the output, and then returns to the object queue loop 17.

As best illustrated by reference to FIG. 34 it should be understood that an external process, not shown, and which may include such programs as "Atlantis", "Sensor", and "Helena" are operable to be accessed by a user, not shown, and which are operable to provide instructions regarding a particular sensor to the library function, which, in turn, transmits the request for information through an operating system module which converts this same information into a format which is understood by the main module and which is set forth in greater detail in Figs. 1 through 33, respectively. The main module is operable to interpret the variables produced by a sensor, and which communicates by means serial or analog protocols and is further operable to interpret the external calling process request for data information from the sensor and thereafter overlay a predetermined adaptable driver which, when adjusted in a predetermined fashion, corresponds to the characteristics of the sensor. As earlier discussed, an adaptable driver is an executable program which is resident on the hard disk of the computer and which may be called up into memory based upon a user command and thereafter employed to provide the requested information from the sensor and which may then be used by the main module. Upon overlaying a predetermined adaptable driver the main module polls, or listens to, the sensor thereby receiving the data information requested, and thereafter transmits the information to a predetermined destination in accordance with the earlier subroutines which were discussed in greater detail in the paragraphs above. As best illustrated in the example which follows, the driver skeleton for a Nellcor N200 pulse oxymeter is provided and which illustrates the type of driver skeleton which is resident within the main module and which provides a means by which a relatively unskilled programmer may use the same driver skeleton and thereafter rapidly interface the main module with a sensor which is foreign to the present device with very minimal amounts of reprogramming.

```
/*
                    HMP MEDICAL INTERFACE BUS

C - DRIVER SKELETON

Driver ID: Nellcor N-200
          Version:
          Date Last Worked on:
          By:
          Comments: This example adds to the main module a driver for
                    the Nellcor N200 pulse oxymeter.
                                                                     */ int_acrtused = 0;

/*
```

C SKELETON EQUATES (do not alter)

```c
#include<drv_equ.h>
#include<var_equ.h>
```

/*

STRUCTURE DEFINITION TO DEVICE (do not alter)

*/

```c
struct REQUEST {
    char mon_req[10];       /* request to mon (10 chars max)    */
    char mon_lreq;          /* real length of request           */
    char mon_ans[5];        /* answer expected from mon         */
    char mon_lans;          /* length of answer to check        */
    char mon_fl4ans;        /* answer to wait for               */
    char mon_filler[2];     /* filler for 20 char in structure  */
                            /* length in mib_equ                */
};
```

/*

COMMUNICATIONS POLLING DEFAULTS (Enter here information)

(do not reorder)

*/

```c
char mon_name[8]     = {"n200c"};     /* name of file (DOS max=8 char)        */
int  mon_poll_int    = 200;           /* tm int for poll freq in 1/100'ths sec*/
int  mon_delay_int   = 40;            /* tm delay between polling and respose */
char mon_baud        = BAUD_9600;     /* baud rate from drv_equ.h             */
char mon_parity      = DB8_S81_NOP;   /* port settings from drv_equ.h         */ char mon_language    = 'C';           /* this driver is in C language         */
char mon_flavor      = 1;             /* 1 = monitoring device                */
char mon_pollable    = 1;             /* 1 = mon pollable, 2 = not pollable   */
char mon_spec_comdef = 0;             /* see manual for explanation           */ char mon_step4hello  = 1;             /* see manual for explanation           */
char mon_numof_steps = 2;             /* see manual for explanation           */
```

/*

STRUCTURE FOR REQUEST TO DEVICE (Enter here information)

*/

```c
char mon_pos4req[8]  = {"REQ_SOT"};   /* string header for request            */
struct REQUEST mon_request[2] = {
    {"S         ",1,"S        ",1,1," "}
    {"R         ",1,"R        ",1,1," "}
```

```c
/*
                    VARIABLES TO READ FROM DEVICE
                        (Enter here information)
                          (do not reorder)

*/ char var_pos4req[8]  = {"VAR_sot"};    /* string header variables/id's
int vars_numof       = 2;
int var_present[2]   = { PULSE, SAO2 };
char vars_id[2]      = {"RS"};

#include,cdrv_fn.h>                    /* c-function library for main module */

*/
                    BEGIN CODE TO DECODE STRING FROM DEVICE
                           (Enter here code...)

INPUT:
        int function_type:   1 = decoding
        int mon_str_len:     Length of str_2decode
        int var_rank:        rank of var to decode eg. SAO2 = 1. (0 based)
        char *str_2decode:   answer from device OUTPUT:
        char result[20]:     decoded string to return to main module FORMAT: 'vvvvv ' variable value in 5 chars
            trailing blank for future use

EQUATES: BUF4ANS_LEN = max length of string from device

*/ char *ov0fn(int function_type,int mon_str_len,int var_rank,char *str_2decode)

{ char *tab[BUF4ANS_LEN];
char result[20];
int i,j;

/* Passing of Arguments */ tab[0] = str_2decode;
for (i = 1; i < mon_str_len && i < BUF4ANS>LEN; i++)
        tab[i] = tab[i-1] + 1;

/* DECODING CODE FOR STRING COMING FROM MON. DEVICE BEGINS HERE */ for (i = 0; i < mon_str_len && i < BUF4ANS_LEN; i++){
        if (*tab[i] == vars_id[var_rank])
            break;

}
```

```
if ( i == mon_str_len) return(buf_error);

result[0] = '0';
result[1] = '0';

for (j=0; j<3; j++)
     result[j+2] = *tab[i+1+j];

result [j+2] = '\0';

return(result);

}
```

As best understood following a study of the example provided above, the step of overlaying and updating a predetermined adjustable driver includes the steps of entering the name of the adaptable driver format in the driver skeleton as provided; providing a polling timer interval for the sensor; entering a timing delay interval for the sensor and which is operable to await the answer of the sensor for each request; providing a baud rate and parity for the sensor being polled; providing the name of the language which is employed by the driver; entering the type of sensor device being polled; determining whether the sensor can be polled or listened to and providing instructions as appropriate; providing special communications instructions to the sensor, if necessary; entering the number of polling requests which must be completed to insure receipt of all data information from the sensor; providing the external process requests to be made to the sensor for each of the steps; providing the variables which are to be read from the sensor; decoding the variables received from the sensor, and delivering same to a predetermined destination. As should be understood, the step of providing the variables which are to be read from the sensor includes providing the number of variables which are to be read from the sensor, and identifying the variables which are to be read from the sensor. In the present case, the pulse and SA02 variables are being received from the present device which is shown in the example.

It should be understood that the inventors have discovered that with respect to medical monitoring devices of the type anticipated to be used with the present invention that, as a general matter, the general format or skeleton of the data information has a basic structure which is quite similar to the skeleton noted in the example above. Therefore, a programmer utilizing the skeleton can very quickly, using only a few lines of code, successfully interface a foreign sensor with the main module. In the present example the inventors have provided the driver skeleton for a Nellcor N200 pulse oxymeter which provides SA02 and pulse to a clinician for diagnostic purposes.

Referring to the example noted above, and more specifically to that portion of the example which is entitled "Communication Polling Defaults" it should be understood that the skeleton is written in C language, although those skilled in the art will readily recognize that assembly language could be used with equal success. In this regard the skeleton of the above-identified Nellcor N200 pulse oxymeter has a means for providing a request to the sensor and which is indicated by the first line of commands in that portion of the skeleton labelled "Structure Definition to Device". Further, the skeleton provides a location where the name of the sensor, and in the present example the designation N200C is entered. The next command provides a means whereby a monitor polling interval may be established. As should be understood, and depending upon the type of sensor involved, a monitor may be available for polling at predetermined intervals as a result of their own inherent engineering characteristics. In this regard, and based upon the characteristics of the sensor, an operator may enter the polling interval frequency for the monitor in question. Further, the next command provides a means for setting a timing delay between the polling request and the response from the monitor. In this regard it should be understood that, in certain instances, and based in large measure on the characteristics of the monitor, or sensor being polled, the monitor may not provide the data instantaneously and thus there may be a time delay. In this instance the time delay would be entered at this location in the skeleton. Further the next two lines of commands includes standard communication settings for both the baud rate of the sensor being polled, as well as the parity for the sensor. These communications parameters are well understood by those skilled in the art. The driver skeleton in the example above provides a means whereby the language of the driver which is providing the communications data may be entered such that the main module can understand how it will call the code overlay. In this regard, and in the example provided, the sensor (Nellcor N200) produces data in C language, and this information is entered at this location in the skeleton.

The driver skeleton provides a means whereby an operator may enter information regarding whether the present sensor under consideration is a monitoring device; a local area network; or further, whether the driver produces information either in a serial or analog format. By entering the appropriate characters as provided in this portion of the skeleton, the operator may adjust the skeleton for those features of the sensor. The next line of commands in the skeleton provide a means by which the operator can enter special communications definitions, and more particularly those communications definitions related to whether the sensor being polled is pollable or non-pollable. As should be understood some sensors produce information at periodic time intervals and cannot be polled by an external calling process. By inserting the appropriate character at this portion of the skeleton the operator may adjust the skeleton as appropriate for these communications parameters. The next line of command relates to special communications definition, and more particularly to the initialization of the sensor being polled. In this regard, it should be understood, that some sensors, based upon their inherent design characteristics, may require specific instructions prior to providing the data information requested. The skeleton therefore provides an operator with a means for adjusting same for those sensors having these characteristics. In addition, the next command in the skeleton provides a means by which an operator may compensate for a multiplicity of steps which may be required in order to cause the same sensor to provide the data information requested. As should be understood, some sensors, based upon their inherent design characteristics, may need to exchange several bits of data and/or provide or receive various instructions from an external calling process prior to transmitting the requested information. In this regard, an appropriate character may be entered at this point in the skeleton to compensate for those shortcomings in the sensor. Finally the last line of instructions provides a means by which the operator may set the number of steps required in order to receive enough information for the handshake. As should be understood certain sensors may be required to be polled a number of times in order to receive all the information requested. In this regard the Nellcor N-200 must receive two requests for information prior to divulging all the information that is, pulse, and SA02, but, as a general matter one request is usually sufficient to complete the handshake.

Referring more particularly to that portion of the skeleton labelled "Structure for request to device", it should be understood that means are provided for requesting data from the sensor. One skilled in the art will recognize the use of the structure described in that portion of the skeleton labelled "Structure request to device". This includes a set of information for requesting data from a sensor. In the present example, the skeleton includes two requests. The first set of information requests the string to send to the sensor. In this regard and in the skeleton of the Nellcor shown above, the string is a "S". The next set of information is its length. In the present example it is a "1". The remainder of the characters are for validating the answer, followed by their number. In the above example, it is an "S", and one character. The "1" following the "S" specifies that the main module will expect an answer for that request.

Referring more particularly to that portion of the example provided above, and which is directed to the variables to read from the device portion, it should be understood that means are provided for reading the variables received from the sensors, and wherein the operator may designate the number of variables to be read. Further the operator may also designate the variables by type. In this instance, the example provides that the variables being read are pulse, and SA02, and which are set forth in the text above. The character identification are designated as R and S, respectively. Finally the example above provides an example of decoding the variables received from the sensor. As should be readily apparent upon a close study of the example, an operator may only be required to enter as little as ten lines of programming in order to complete a foreign sensor driver as appropriate for the main module.

Therefore the method for interpreting variables produced by a sensor and which communicates by means of serial or analog protocol can be employed in a wide variety of operative environments, and can be manufactured and purchased at moderate cost when compared with related prior art software devices, is different sensors having different communications parameters and which further is highly efficient in operation and reduces to an absolute minimum the problems associated with the assimilation of clinical information from diverse sources and which are designed for substantially identical purposes.

Although the invention has been herein shown and described in what is conceivably the most practical and preferred embodiment, it is recognized that departures may be made therefrom within the scope of the invention which is not to be limited to the illustrative details disclosed.

Having described our invention, what we claim is new and desire to secure by Letters Patent is:

1. A software engine for interpreting variables produced by a plurality of sensors which communicate by means of serial, analog or local area network protocols, the software engine comprising:
   means for interpreting an external process request for data information which includes the variable produced by the sensor, and wherein the external process request is an independently executable software program which includes a piece of software code which generates a message in a predetermined format requesting from the software engine the delivery of data which is in a specific format and syntax, and wherein the independently executable software program in otherwise unfamiliar with the software engine and which further includes:
   a. means for interfacing with an operating system to determine if an appropriate operating system is present and to execute the necessary memory and disk management functions such that the software engine can operate, the software engine otherwise being operating system independent, and wherein the interface means is included in a main module;
   b. means for creating a mailbox which is adapted to exchange information with the external process request, and
   c. means for opening an object queue loop, and wherein the object queue loop identifies an object type and initiates a predetermined process with the individual sensors requested by the external process;
   means for overlaying a predetermined adaptable driver, which, when adjusted in a predetermined fashion, corresponds to the data characteristics of the individual sensors and wherein the adaptable driver decodes the variables requested by the external process request;
   means for polling or listening to the individual sensors, thereby receiving the data information requested by the external process request, and wherein the data information received is in a predefined format, and in any syntax; and
   means for transmitting the data information generated by the individual sensors to a predetermined destination.

2. A software engine as claimed in claim 1 and wherein the object type includes mailbox, timer, and keyboard objects, and wherein the software engine includes predetermined processes which correspond with the mailbox, timer, and keyboard objects.

3. A software engine as claimed in claim 2 and wherein the mailbox process includes,
   means for initiating communications with the external process;
   means for determining the characteristics of the driver employed by the sensor;
   means for overlaying and updating the predetermined adaptable driver format to substantially correspond to the characteristics of the sensor;
   means for polling or listening to the sensor thereby receiving the data information requested;

means for decoding the variable requested by the external process;

means for transmitting the decoded information to a predetermined destination directed by the external process; and means for returning to the object queue loop.

4. The software engine as claimed in claim 2 and wherein the timer process includes a polling timer process and a delay timer process.

5. A software engine as claimed in claim 4 and wherein the polling timer process includes, means for starting the polling timer;

means for determining the characteristics of the driver associated with the polling request;

means for executing the first polling request received from the external process;

means for actuating a delay timer;

means for transmitting the information received from the first polling request to a predetermined destination which corresponds to the external process request upon deactivation of the delay timer; and means for returning to the object queue loop.

6. A software engine as claimed in claim 4 and wherein the delay timer process includes, means for determining if conditions for polling the sensor have been met;

means for continuing communication with the sensor;

means for transmitting the information received from the sensor to a predetermined destination; and means for returning to the object queue loop.

7. A software engine as claimed in claim 2 and wherein the keyboard process includes a status process, and a keyboard interaction process, and wherein the status process includes, means for determining the type of input or driver;

means for selecting an appropriate data format which corresponds with the type of input or driver;

means for displaying the given data format for the given input or driver; and means for returning to the object queue loop.

8. A software engine as claimed in claim 7 and wherein the keyboard interaction process includes, means for determining the type of request from a user as an external process;

means for identifying the type of driver which corresponds to the user request;

means for loading a driver code overlay which corresponds with the type of driver identified;

means for requesting a direction and format for the output; and means for returning to the object queue loop.

9. A method as claimed in claim 2 and wherein the means for overlaying the predetermined adaptable driver includes, means for loading the adaptable driver;

means for ascertaining the communication parameters of the sensor; and means for modifying the predetermined adaptable driver with the variables which substantially correspond with the variables requested by the external process and which correspond with the sensor being polled.

10. A software engine as claimed in claim 2 and wherein the means for overlaying the predetermined adaptable driver includes, means for entering the name of the adaptable driver format;

means for providing a polling timer interval for the sensor;

means for entering a timing delay interval for the polling timer and which is operable to delay the polling requests to the sensor;

means for providing a baud rate and parity for the sensor being polled;

means for providing the name of the language which is employed by the sensor;

means for entering the type of sensor device being polled;

means for determining whether the sensor can be polled, or listened to, and providing instructions as appropriate;

means for providing special communication instructions to the sensor, if necessary;

means for entering the number of polling requests which must be completed to ensure receipt of all the data information from the sensor;

means for providing the variables which are to be read from the sensor; and means for decoding the variables received from the sensor and delivering same to a predetermined destination.

11. A software engine as claimed in claim 10 and wherein the means for providing special communications instructions includes, means for initialization of the sensor being polled;

means for establishing communication with the sensor being polled; and means for polling the sensor a predetermined number of times to receive all the data information produced by same.

12. A software engine as claimed in claim 11 and wherein the means for providing the variables which are to be read from the sensor include, means for providing the number of variables which are to be read from the sensor; and means for identifying the variables which are to be read from the sensor.

13. A software engine for interpreting data information which includes variables produced by a plurality of sensors which communicate by means of serial, analog or local area network protocols, and wherein the software engine operates at run time, in combination with an operating system, to execute the necessary memory and/or disk management functions such that the software engine can operate, the software engine comprising:

means for interpreting an external process request for data information from the sensors and wherein the external process request is an independently executable software program which runs simultaneously and independently with respect to the software engine, and which further has an operating system interface module which executes the necessary memory and disk management functions such that the software engine can operate, the software engine otherwise being operating system independent, and wherein the independently executable software program includes a piece of software code which generates a message in a predetermined format requesting from the software engine the delivery of data which is in a predetermined format and syntax, and wherein the interpreting means includes a module disposed in data receiving relation relative to the external process request, and which is operable to initiate an object queue loop which identifies different object types including a mailbox through which data information is exchanged with the external process, and a timer which regulates the frequency of data exchanges with the individual sensors requested by the external process, and wherein the module further processes the data exchanges with the individual sensors;

means for overlaying a predetermined adaptable driver which, when adjusted in a predetermined fashion by employing specific functions of the operating system, corresponds to the data characteristics of the individual sensors, and wherein the predetermined adaptable driver to be overlayed includes a driver skeleton which has a decoding area, and wherein an operator, prior to overlaying the predetermined adaptable driver, supplies data to the driver skeleton which includes, a name for the adaptable driver;

a polling timer interval for the individual sensors;

a timing delay interval which is provided to the module and which determines the time interval with which the module must return to the individual sensors to receive all the data requested by the external process;

a baud rate, and parity, for the individual sensors being polled by way of serial communications;

a name of the language which is employed by the individual sensors;

the type of sensor device being polled or listened to, including serial, analog, or local area networks;

instructions regarding whether the individual sensors can be polled, or listened to;

any special communication instructions to the individual sensors;

the number of polling requests which must be completed to ensure receipt of all the data information from the individual sensors;

the variables which are to be read from the individual sensors; and the decoding area of the driver skeleton which decodes the variables read from the individual sensors;

means for polling or listening to the individual sensors thereby receiving the data information requested by the external process request, and wherein the data information received is in a predetermined protocol, and in any syntax, and wherein the driver decoding area decodes the variables requested by the external process request; and means for routing the variables generated by the individual sensors, and which have been decoded by the driver decoding area, to a predetermined destination, or to the requesting external process, as appropriate.

14. A software engine which operates in combination with a computer having a disk operating system, and wherein the software engine is operable to interpret variables produced from a plurality of remote sensors which communicates by serial, analog or local area network protocols, and wherein an external process requests data information from selected sensors and the software engine directs the requested information to a predetermined destination, the software engine comprising:

a library function which can be accessed from the external process, and wherein the library function executes a plurality of commands which can be requested by an operator, and wherein an operator issues commands through the library function regarding the particular remote sensor from which data information is requested;

a main module including an operating system interface module, and wherein the operating system interface module is operating system dependent, and disposed in data receiving relation relative to the library function, and wherein the main module includes a memory which stores a plurality of drivers which are operable to interpret the external process request for information, and wherein the library function transmits the external process request for information and converts this external process request into a format which is understood by the main module, and wherein the main module is operable upon the request of the external process, to determine whether an appropriate operating system is present to execute the necessary memory and disk management functions such that the software engine can operate but which is otherwise operating system independent, create a mailbox through which data information is exchanged with the external process, and initiate an object queue loop which identifies predetermined object types, and wherein the main module initiates a process unique to each of the object types, and the particular remote sensor requested by the external process;

means for overlaying a predetermined adaptable driver which, when adjusted in a predetermined fashion by employing specific functions of the operating system, corresponds to the characteristics of the particular sensor, and wherein the adaptable driver called up from the memory of the main module and overlayed includes a driver skeleton which has a decoding area, and wherein the driver skeleton may be adjusted by an operator, and the decoding area employed to decode the variables produced by the particular remote sensor, the operator supplying information to the driver skeleton which includes, a name for the adaptable driver;

a polling timer interval for the particular sensor;

a timing delay interval which is provided to the main module and which determines the time interval with which the main module must return to the particular sensor to receive all the data requested by the external process;

a baud rate, and parity, for the particular sensor being polled by way of serial communications;

a name of the language which is employed by the operator in the decoding area of the particular sensor;

the type of sensor being polled or listened to;

instructions whether the particular sensor can be polled or listened to, as appropriate;

any special communication instructions to the particular sensor, as appropriate;

the number of polling requests which must be completed to ensure receipt of all data information from the particular sensor;

the variables which are to be read from the particular sensor; and the decoding area of the driver skeleton and which decodes the variables read from the particular sensor;

means for polling or listening to the particular sensor thereby receiving the variables which have been decodes by the decoding area of the updated driver skeleton; and means for routing the decoded variables to a predetermined destination, or to the requesting external process, as appropriate.

* * * * *

UNITED STATES PATENT AND TRADEMARK OFFICE
CERTIFICATE OF CORRECTION

PATENT NO. : 5,161,222
DATED : November 3, 1992
INVENTOR(S) : Montejo et al.

It is certified that error appears in the above—identified patent and that said Letters Patent is hereby corrected as shown below:

Column 13, line 47, after the numeral 133, insert --.--;

Column 15, line 5, after the numeral 176, insert --.--;

Column 19, line 35, after the numeral 17, insert --.--;

Column 27, line 61, after the words "devices, is" insert --highly efficient in operation and is operable to facilitate the rapid assimilation of sensor information from a variety of--;

Column 28, line 13, delete the word --variable-- and insrt --variables--.

Signed and Sealed this

Twenty-eighth Day of September, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,161,222
DATED : November 3, 1992
INVENTOR(S) : Leopoldo S. Montejo and Martine Pean It is certified that error appears in the above-identified patent and that said Letters Patent is hereby corrected as shown below:

Column 28,
Line 21, delete the word "in", and insert -- is --.

Column 33,
Line 3, delete the word "decodes", and insert -- decoded --.

Signed and Sealed this

Twentieth Day of September, 2005

JON W. DUDAS
*Director of the United States Patent and Trademark Office*